US012788564B2

(12) United States Patent
Marquez et al.

(10) Patent No.: US 12,788,564 B2
(45) Date of Patent: Nov. 10, 2026

(54) TESTING APPARATUS FOR PROSTHETIC DEVICE

(71) Applicant: EDWARDS LIFESCIENCES CORPORATION, Irvine, CA (US)

(72) Inventors: Salvador Marquez, Foothill Ranch, CA (US); Lynn T. Dang, Huntington Beach, CA (US); Javier A. Sanguinetti, Irvine, CA (US); Emily Cheng Zhou, Aliso Viejo, CA (US); Gary Alan Breitbach, Washougal, WA (US)

(73) Assignee: Edwards Lifesciences Corporation, Irvine, CA (US)

( * ) Notice: Subject to any disclaimer, the term of this patent is extended or adjusted under 35 U.S.C. 154(b) by 536 days.

(21) Appl. No.: 18/465,920

(22) Filed: Sep. 12, 2023

(65) Prior Publication Data

US 2023/0414359 A1 Dec. 28, 2023

Related U.S. Application Data

(60) Division of application No. 17/156,455, filed on Jan. 22, 2021, now Pat. No. 11,786,374, which is a (Continued)

(51) Int. Cl.
*A61F 2/24* (2006.01)
*A61F 2/76* (2006.01)
*F16K 37/00* (2006.01)

(52) U.S. Cl.
CPC .............. *A61F 2/2472* (2013.01); *A61F 2/76* (2013.01); *F16K 37/0091* (2013.01); *A61F 2/2418* (2013.01); *A61F 2002/7635* (2013.01)

(58) Field of Classification Search
None
See application file for complete search history.

(56) References Cited

U.S. PATENT DOCUMENTS

| | | | |
|---|---|---|---|
| 4,381,663 | A | 5/1983 | Swanson |
| 4,450,710 | A | 5/1984 | Nettekoven |

(Continued)

FOREIGN PATENT DOCUMENTS

| | | | |
|---|---|---|---|
| CN | 102415919 | A | 4/2012 |
| CN | 203417276 | U | 2/2014 |
| CN | 104248478 | A | 12/2014 |
| JP | 2016002438 | A | 1/2016 |

OTHER PUBLICATIONS

Iyengar AKS, Sugimoto H, Smith DB, Sacks MS. Dynamic in vitro quantification of bioprosthetic heart valve leaflet motion using structured light projection. Ann Biomed Eng. Nov. 2001;29(11):963-73. doi: 10.1114/1.1415523. PMID: 11791679. (Year: 2001).*

(Continued)

*Primary Examiner* — Siamak Harandi
*Assistant Examiner* — Annie H Pham
(74) *Attorney, Agent, or Firm* — Snell & Wilmer

(57) ABSTRACT

A testing apparatus is disclosed herein for testing properties of a prosthetic device. The testing apparatus may comprise a dual-drive pulsatile flow tester with the ability to determine coaptation of valve leaflets of a prosthetic device. The testing apparatus may be able to test prosthetic heart valves and reproduce physiological conditions of a prosthetic heart valve.

20 Claims, 19 Drawing Sheets

Related U.S. Application Data continuation of application No. 16/257,982, filed on Jan. 25, 2019, now Pat. No. 10,898,329.

(56) References Cited

U.S. PATENT DOCUMENTS

| | | | |
|---|---|---|---|
| 4,546,642 | A | 10/1985 | Swanson |
| 4,598,579 | A | 7/1986 | Cummings et al. |
| 4,682,491 | A | 7/1987 | Pickard |
| 4,972,721 | A | 11/1990 | Conti |
| 5,176,153 | A | 1/1993 | Eberhardt |
| 5,272,909 | A | 12/1993 | Nguyen et al. |
| 5,284,423 | A | 2/1994 | Holdsworth et al. |
| 5,327,774 | A | 7/1994 | Nguyen et al. |
| 5,531,094 | A | 7/1996 | More et al. |
| 5,546,820 | A | 8/1996 | Eberhardt et al. |
| 5,584,878 | A | 12/1996 | Love et al. |
| 5,670,708 | A | 9/1997 | Vilendrer |
| 5,671,718 | A | 9/1997 | Curran et al. |
| 5,768,443 | A | 6/1998 | Michael et al. |
| 5,792,603 | A | 8/1998 | Dunkelman et al. |
| 5,816,096 | A | 10/1998 | Ng et al. |
| 6,062,075 | A | 5/2000 | Ritz et al. |
| 6,245,105 | B1 | 6/2001 | Nguyen et al. |
| 6,363,169 | B1 | 3/2002 | Ritter et al. |
| 7,063,942 | B2 | 6/2006 | Dancu et al. |
| 7,860,298 | B2 | 12/2010 | Leikas et al. |
| 8,170,329 | B2 | 5/2012 | Seko et al. |
| 8,230,717 | B2 | 7/2012 | Matonick |
| 8,584,538 | B2 | 11/2013 | Mccloskey et al. |
| 8,617,774 | B2 | 12/2013 | Kerwien et al. |
| 8,800,348 | B2 | 8/2014 | Lee |
| 9,186,224 | B2 | 11/2015 | McCloskey et al. |
| 9,237,935 | B2 | 1/2016 | Mccloskey et al. |
| 9,662,211 | B2 | 5/2017 | Hodson et al. |
| 9,895,226 | B1 | 2/2018 | Harari et al. |
| 10,105,227 | B2 | 10/2018 | Dingmann et al. |
| 10,350,069 | B2 | 7/2019 | Dingmann et al. |
| 10,627,315 | B2 | 4/2020 | Conti et al. |
| 10,779,946 | B2 | 9/2020 | Kislev et al. |
| 11,065,122 | B2 | 7/2021 | Harari et al. |
| 11,238,613 | B2 | 2/2022 | Doganis |
| 11,252,395 | B2 | 2/2022 | Zhao et al. |
| 2003/0066338 | A1 | 4/2003 | Michalsky et al. |
| 2003/0110830 | A1 | 6/2003 | Dehdashtian et al. |
| 2003/0125804 | A1 | 7/2003 | Kruse et al. |
| 2004/0016301 | A1 | 1/2004 | Moreno et al. |
| 2006/0230814 | A1 | 10/2006 | Keeble |
| 2007/0185534 | A1 | 8/2007 | Conti et al. |
| 2008/0047356 | A1 | 2/2008 | Black et al. |
| 2010/0225478 | A1 | 9/2010 | Mccloskey et al. |
| 2010/0242620 | A1 | 9/2010 | Lorenz et al. |
| 2010/0291524 | A1 | 11/2010 | Iwasaki et al. |
| 2011/0259439 | A1 | 10/2011 | Neerincx |
| 2013/0261994 | A1 | 10/2013 | Raz et al. |
| 2014/0011170 | A1 | 1/2014 | Nickel et al. |
| 2014/0076029 | A1 | 3/2014 | Lee |
| 2014/0099620 | A1 | 4/2014 | Lee |
| 2014/0127795 | A1 | 5/2014 | Dancu et al. |
| 2016/0027345 | A1 | 1/2016 | Carson et al. |
| 2017/0051736 | A1 | 2/2017 | Okayama et al. |
| 2017/0252164 | A1 | 9/2017 | Dingmann et al. |
| 2018/0018904 | A1 | 1/2018 | Okayama et al. |
| 2020/0046500 | A1 | 2/2020 | Lee |
| 2020/0237515 | A1 | 7/2020 | Marquez et al. |
| 2022/0044057 | A1 | 2/2022 | Ganesan et al. |

OTHER PUBLICATIONS

Susin FM, Espa S, Toninato R, Fortini S, Querzoli G. Integrated strategy for in vitro characterization of a bileaflet mechanical aortic valve. Biomed Eng Online. Feb. 16, 2017;16(1):29. doi: 10.1186/s12938-017-0314-2. PMID: 28209171; PMCID: PMC5314609. (Year : 2017).*

Marassi, M., et al. "Cardiac valve prosthesis flow performances measured by 2D and 3D-stereo particle image velocimetry." Experiments in Fluids 36.1 (2004): 176-186. (Year: 2004).*

Gao, Bruce Z., et al. "Bioprosthetic heart valve leaflet deformation monitored by double-pulse stereo photogrammetry." Annals of Biomedical Engineering 30.1 (2002): 11-18. (Year: 2002).*

Condurache AP, Hahn T, Scharfschwerdt M, Mertins A, Aach T. Video-based measuring of quality parameters for tricuspid xenograft heart valve implants. IEEE Trans Biomed Eng. Dec. 2009;56(12):2868-78. doi: 10.1109/TBME.2008.2001290. Epub Jun. 20, 2008. PMID: 19272952. (Year: 2009).*

Abbasi, Mostafa, et al. "High resolution three-dimensional strain mapping of bioprosthetic heart valves using digital image correlation." Journal of biomechanics 76 (2018): 27-34. (Year: 2018).*

The Wayback Machine: "Table Tent, 4 x 6-in, Acrylic, 6-Sided," Katom, Sep. 21, 2015, 1 Page, Retrieved from URL: https://web.archive.org/web/20150921020226/https://www.katom.com/229-40606.html.

Xinhuanet: "3D Heart Models Help Optimize Surgery Options for Aortic Valve Replacement," New China, Mar. 6, 2018, 4 Pages, Retrieved from URL: http://www.xinhuanet.com/english/2018-03/06/c_137020512.htm.

"3D heart models help optimize surgery options for aortic valve replacement," New China, <http://www.xinhuanet.com/english/2018-03/06/c_137020512.htm>, Mar. 6, 2018.

"Durapulse Enables Accelerated Heart Valve Testing," Biotech Equipment Update, vol. 22, Issue 10, Wordwide Videotex, Boston, US, Oct. 1, 2014.

"Heart valve pulse duplicator system," BDC Laboratories, <http:/www.bdclabs.com/testing-equipment/pulse-duplicator-system/>, Sep. 6, 2015.

"Heart Valve Testing: Steady flow hydrodynamic performance evaluation," Protomed Labs, <http://www.protomedlabs.com/medical-devices-testings/device-testings/heart-valve-testing-steady-flow/>.

"Hydrodynamic Testing," Vivitro Labs, Inc., <http://vivitrolabs.com/services/hydrodynamic-testing/>, printed Sep. 6, 2015.

"Pulsatile flow testing in the CVE pulse duplicator," Institute of Applied Medical Engineering ("AME"), Sep. 6, 2015.

ElectroForce Linear Motor, <http://electroforce.tainstruments.com/electroforce/en_us/web/linear_motor_technology/page.html>, printed Sep. 2, 20155.

Fisher, Jr. et al., "Design of a function test apparatus for prosthetic heart valves. Initial results in the mitral position," Clinical Physics and Physiological Measurement, vol. 7, No. 1, Department of Cardiac Surgery, Glasgow, UK, 1986.

Lee, Denis et al., "In Vitro Testing of Venous Valves," Slide Forum 12, Vascular Prosthesis II, Trans AM Soc Artif Intern Organs, vol. XXXVII, Asaio Transactions, 1991.

List of MITL Products, Medical Implant Testing Lab, <http://medicalimplanttestinglab.com/products.html#sft>, printed Sep. 6, 2015.

Pulsatile Pumps, BDC Laboratories, <http://www.bdclabs.com/testing-equipment/pulsatile-pump-systems/>, printed 2018 May 2017.

Rittgers, Stanley E et al., "Physiologically-based testing system for the mechanical characterization of prosthetic vein valves," BioMedical Engineering Online 2007, 6:29, doi: 10.1186/1475-925X-6-29, Department of Biomeidcal Engineering, The University of Akron, Akron OH, Jul. 13, 2007.

Tsai, William et al., "Flow pumping system for physiological waveforms," Med Biol Eng Comput (2010) 48:197-201, DOI: 10.1007/s11517-009-0573-6, Department of Mechanical Engineering, University of California, Berkeley, Berkeley, CA.

Umezu, Mitsuo et al., "Hydrodynamic Characteristics of Newly-Developed Prosthetic Heart Valves by the Use of Several Types of In-Vitro Test Systems," St. Vincent's Hospital, Darlinghurst, NSW, Australia, 1989.

Wright, J.T.M. et al., "An improved method for determining the flow characteristics of prosthetic mitral heart valves, " Thorax (1971), 26, 81, Bio-engineering and Medical Physics Unit, Department of Surgery, University of Liverpool and the Cardio-thoracic Surgical Centre, Broadgreen Hospital, Liverpool.

* cited by examiner

TESTING APPARATUS FOR PROSTHETIC DEVICE

CROSS REFERENCE TO RELATED APPLICATIONS

This application is a divisional of U.S. patent application Ser. No. 17/156,455, filed Jan. 22, 2021, which is a continuation of U.S. patent application Ser. No. 16/257,982, filed Jan. 25, 2019, now U.S. Pat. No. 10,898,329, the entire disclosure of each of which is incorporated by reference for all purposes.

BACKGROUND

Apparatuses have been utilized to measure performance of prosthetic devices. Such prosthetic devices may include prosthetic heart valves or other prosthetic devices. For prosthetic heart valves or other devices that allow for flow therethrough (e.g., stents or the like), the testing apparatuses have generally measured flow through the prosthetic device in a closed loop system. A pump or the like has passed test fluid through the prosthetic device in a steady flow to determine the amount of flow of the device and pressure gradient across the device.

Such apparatuses, however, may not accurately model the performance of the prosthetic device under physiological conditions. Testing under physiological conditions may beneficially allow for a more accurate determination of performance of the prosthetic device when implanted.

Such apparatuses may also be difficult and expensive to maintain and use. Such apparatuses may also have a large size to accommodate a large pump and flow loop.

It may thus be desirable to provide a testing apparatus capable of testing a prosthetic device under physiological conditions and with a simplified design.

SUMMARY

A testing apparatus, and methods and devices, are disclosed herein. The testing apparatus may be configured to measure properties of a prosthetic device, which may comprise a prosthetic valve. The prosthetic valve may comprise a prosthetic heart valve or other form of prosthetic valve. The testing apparatus may be configured to determine flow properties of the prosthetic valve (such as effective orifice area) as well as leaflet coaptation and/or leakage of the prosthetic valve.

The testing apparatus may comprise a dual-drive pulsatile testing apparatus. The testing apparatus may be configured to measure properties of prosthetic devices under physiological conditions. For a prosthetic heart valve, the physiological conditions may include the pumping of the human heart including systole and diastole phases.

A calibration device is disclosed herein. The calibration device may be utilized to determine a scaling between an image distance and real distance, to account for possible optical distortions of views of prosthetic valve leaflets, and to account for the cylindrical geometry of prosthetic heart valves.

Embodiments of the present disclosure may include a testing apparatus for a prosthetic valve. The testing apparatus may include a flow channel having a first end portion and a second end portion, and configured to hold a test fluid. A retainer may be configured to hold the prosthetic valve within the flow channel. A first fluid driver may be coupled to the first end portion of the flow channel and configured to move to flow the test fluid through the prosthetic valve in an outflow direction of the prosthetic valve, and configured to provide a pressure of the test fluid on an inflow side of the prosthetic valve. A second fluid driver may be coupled to the second end portion of the flow channel and configured to move to flow the test fluid through the prosthetic valve in the outflow direction of the prosthetic valve, and configured to provide a pressure of the test fluid on an outflow side of the prosthetic valve. A controller may be configured to move the first fluid driver and the second fluid driver to flow the test fluid through the prosthetic valve in the outflow direction of the prosthetic valve when the prosthetic valve is in an open state. The controller may be configured to operate the first fluid driver to provide a pressure profile of the test fluid on the inflow side of the prosthetic valve when the prosthetic valve is in a closed state. The controller may be configured to operate the second fluid driver to provide a pressure profile of the test fluid on the outflow side of the prosthetic valve when the prosthetic valve is in the closed state.

Embodiments of the present disclosure may include a method. The method may include providing a prosthetic valve in a flow channel of a testing apparatus, the testing apparatus including a first fluid driver coupled to a first end portion of the flow channel and a second fluid driver coupled to a second end portion of the flow channel, the flow channel including test fluid positioned therein. The method may include operating the first fluid driver and the second fluid driver to flow the test fluid through the prosthetic valve in an outflow direction of the prosthetic valve when the prosthetic valve is in an open state. The method may include operating the first fluid driver to provide a pressure profile of the test fluid on an inflow side of the prosthetic valve when the prosthetic valve is in a closed state. The method may include operating the second fluid driver to provide a pressure profile of the test fluid on an outflow side of the prosthetic valve when the prosthetic valve is in the closed state.

Embodiments of the present disclosure may include a calibration device for use in a prosthetic device testing apparatus. The calibration device may include a plurality of walls spaced from each other, and at least one indicator on at least one of the plurality of walls indicating a position on the respective wall.

Embodiments of the present disclosure may include a method. The method may include determining a scaling between an image distance and a real distance based on one or more images of a calibration device having a plurality of walls extending outward from each other and having a defined real distance between portions of the calibration device. The method may include determining a property, based on the scaling, of one or more leaflets of a prosthetic valve shown in one or more images.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
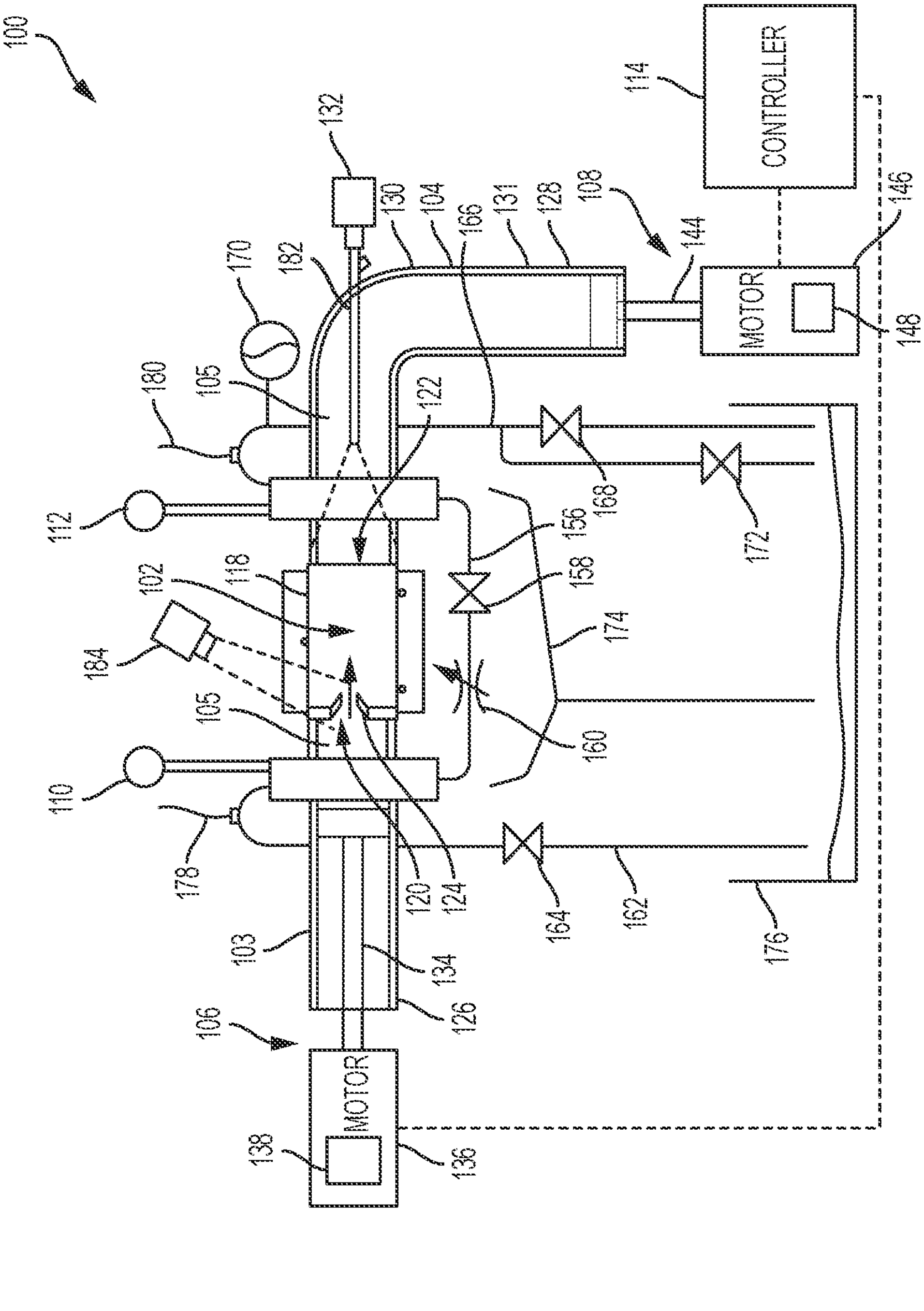
FIG. 1 illustrates a schematic view of a testing apparatus according to an embodiment of the present disclosure.

FIG. 1 illustrates a schematic view of a testing apparatus 100 according to an embodiment of the present disclosure. The testing apparatus 100 may include a test chamber 102, fluid conduits 103, 104 defining a flow channel 105, a first fluid driver 106, a second fluid driver 108, a first pressure sensor 110, a second pressure sensor 112, and a controller 114.

Figure 2:
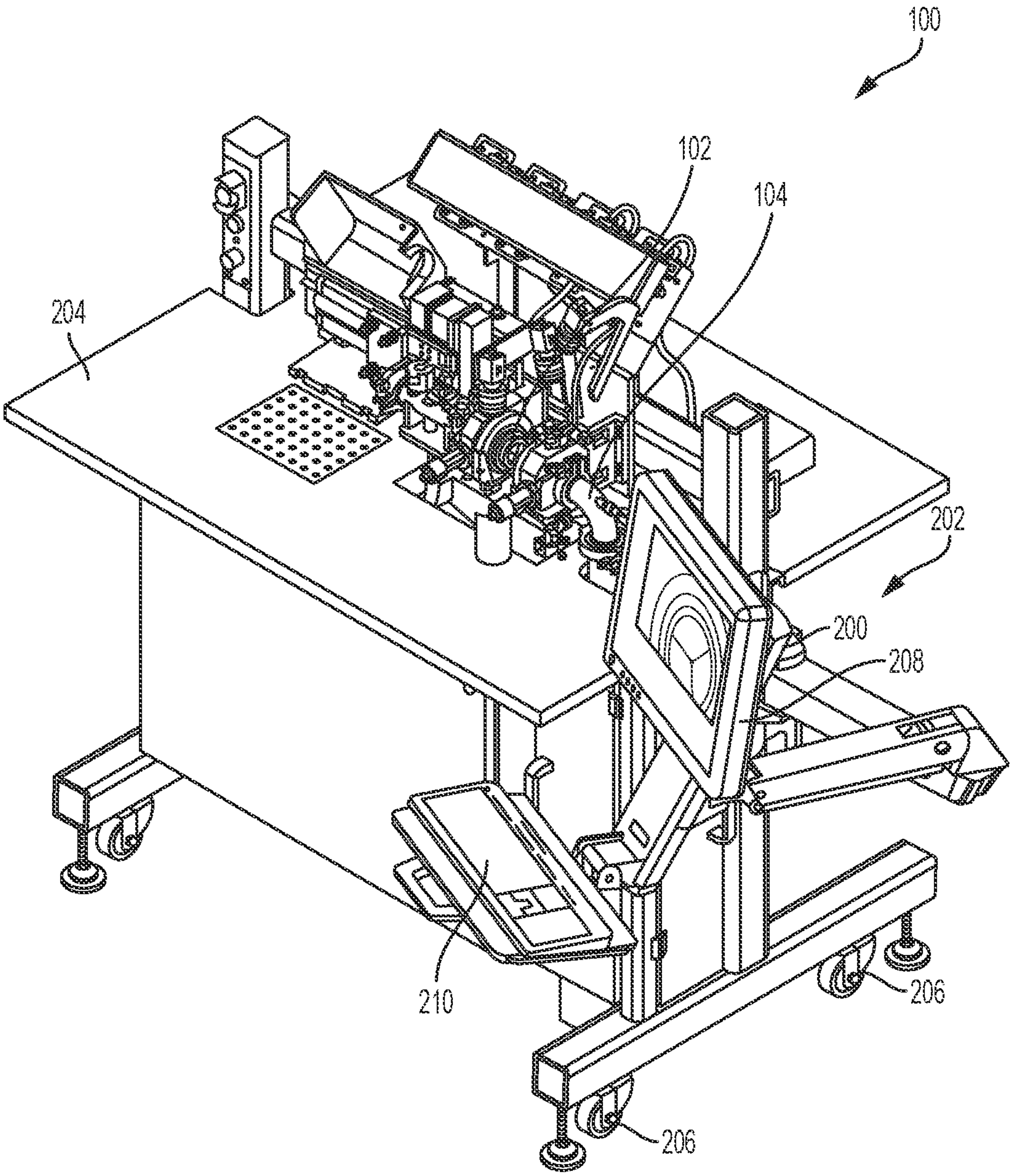
FIG. 2 illustrates a perspective view of a testing apparatus according to an embodiment of the present disclosure.

FIG. 2 illustrates a perspective view of an implementation of the testing apparatus 100. The testing apparatus 100 may include a support structure 200 and a control terminal 202.

Referring back to FIG. 1, the test chamber 102 may include an internal cavity 300 (marked in FIG. 3) that is surrounded by a wall 118. The wall 118 may form the outer surface of the test chamber 102 and a portion or all of the wall 118 may be made of an optically transparent material or otherwise light transmissive material such that the contents of the internal cavity 300 are visible from outside of the test chamber 102. The test chamber 102 may include an opening 120 at a first end of the test chamber 102 and may include an opening 122 at a second opposite end of the test chamber 102. The openings 120, 122 may allow the test chamber 102 to be in fluid communication with respective adjacent portions of the flow channel 105.

The test chamber 102 may be configured to receive a prosthetic device 124 for testing by the testing apparatus 100. The prosthetic device 124 may comprise an implant, which may include a medical implant for implantation within a patient's body. The prosthetic device 124 may comprise a prosthetic valve, which may include a prosthetic heart valve for implantation within a patient's heart. The prosthetic device 124 may be a one-way valve, and as marked in FIG. 1, may be configured to allow for flow in the rightward direction (also referred to as the downstream or outflow direction) in the schematic shown in FIG. 1. The prosthetic device 124 may be a prosthetic aortic valve, or a prosthetic mitral valve, or in other embodiments may be other forms of valves. Such other valves may include valves for controlling flow through another portion of a patient's body such as another portion of the patient's vasculature. In other embodiments, other forms of prosthetic devices such as stents or other prosthetic devices may be utilized.

Figure 3:
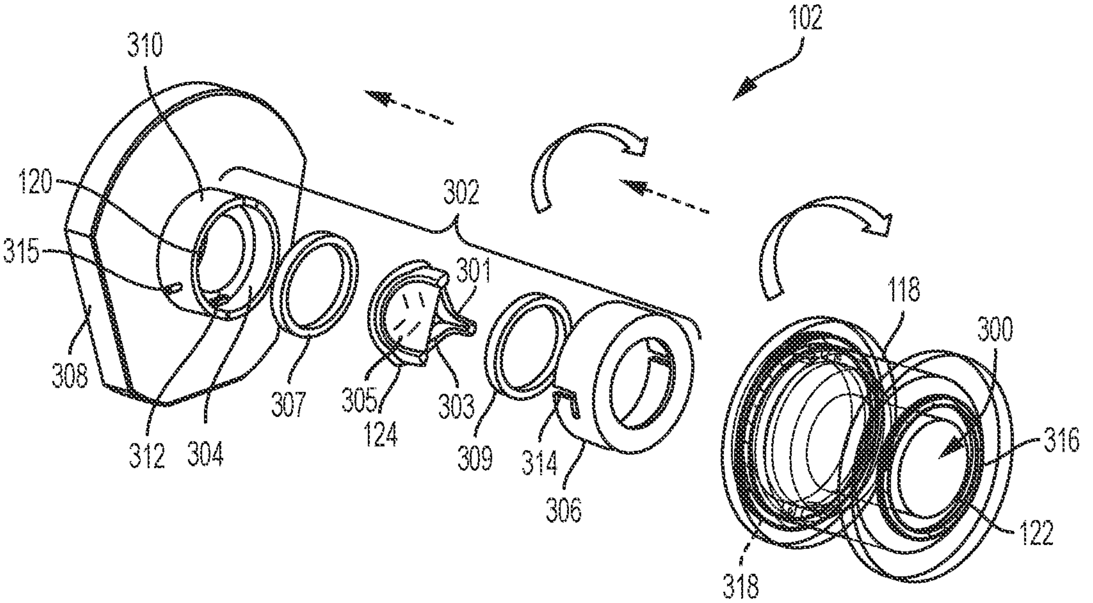
FIG. 3 illustrates a perspective expanded view of a test chamber according to an embodiment of the present disclosure.

FIG. 3 illustrates an expanded perspective view of the test chamber 102. The test chamber 102 may include a retainer 302 configured to hold the prosthetic device 124 in position within the test chamber 102 and within the flow channel 105. The prosthetic device 124 as shown in FIG. 3 may comprise a one-way prosthetic heart valve, having a plurality of leaflets. The prosthetic device 124 as shown in FIG. 3 includes three leaflets 301, 303, 305, although in other embodiments a different number of leaflets may be utilized.

The retainer 302 may include a recess 304 and a securing ring 306. In other embodiments, other forms of retainers may be utilized, for example a clip, clamp, or other form of retainer may be utilized. The recess 304 may be coupled to a mounting plate 308. The retainer 302 may include gaskets 307, 309 for being positioned between the prosthetic device 124 and the respective mounting plate 308 and securing ring 306. The mounting plate 308 may be configured to be positioned within the path of the flow channel 105. The mounting plate 308 may include the opening 120 for fluid communication with the flow channel 105.

The recess 304 may be positioned centrally in the mounting plate 308 and may be configured to receive the prosthetic device 124. The recess 304 may be surrounded by a wall 310 configured to extend around an outer surface of the prosthetic device 124 when the prosthetic device 124 is coupled to the retainer 302. The recess 304 may have an opening 312 that allows for fluid communication with the opening 120 and the flow channel 105, and allows fluid flow through the prosthetic device 124 when the prosthetic device 124 is coupled to the retainer 302.

The securing ring 306 may be configured to lock onto the wall 310 surrounding the recess 304 to secure the prosthetic device 124 between the mounting plate 308 and the securing ring 306. The securing ring 306 may include a lock channel 314 on a sidewall of the securing ring 306 that locks with a locking structure 315 of the wall 310. The securing ring 306 may rotate to lock to the locking structure 315. The securing ring 306 may be configured to extend over the outer surface of the wall 310, with the prosthetic device 124 sandwiched between the gaskets 307, 309, the securing ring 306 and the mounting plate 308. The securing ring 306 may be unlocked from locking structure 315 and removed from the mounting plate 308 to release the prosthetic device 124 from the retainer 302.

The wall 118 and internal cavity 300 of the test chamber 102 are shown in FIG. 3. The wall 118 may have a cylindrical shape extending around the internal cavity 300. The internal cavity 300 may comprise a portion of the flow channel 105 for the test fluid to flow through. As shown, the wall 118 may be optically transparent or otherwise light transmissive such that the contents of the internal cavity **30*o* are visible from outside of the test chamber 102. The test chamber 102 may comprise a viewing chamber for viewing the prosthetic device 124. In an embodiment in which the prosthetic device 124 is a prosthetic heart valve, the leaflets and coaptation of the leaflets of the prosthetic heart valve may be visible through the wall 118 and may be viewed with cameras of a camera system of the testing apparatus 100. The wall 118 may include the opening 122 at the second opposite end of the test chamber 102 for fluid communication with the adjacent portion of the flow channel 105**.

The wall 118 may include a seal 316 at a first end for sealing the connection of the wall 118 with an adjacent mount surface of the testing apparatus 100, and may include a seal 318 at an opposite second end of the wall 118 for sealing a connection with the mounting plate 308.

In assembly, the gasket 307 may be inserted into the recess 304 of the mounting plate 308 and then the prosthetic device 124 may be inserted into the recess 304. The gasket 309 may then be placed upon the prosthetic device 124. The securing ring 306 may be coupled to the locking structure 315 of the wall 118 to secure the prosthetic device 124 in position to the mounting plate 308. The wall 118 of the test chamber 102 may then be coupled to the mounting plate 308 with the prosthetic device 124 positioned within the internal cavity 300. The wall 118 may be coupled to the mounting plate 308 by being slid axially towards the mounting plate 308 and then rotated to lock with the locking structure 315. The prosthetic device 124 may be surrounded by the wall 118 and may be visible through the wall 118. Upon insertion of the test chamber 102 between the fluid conduits 103, 104, fluid flow may pass through the prosthetic device 124 through the openings 120, 312 and opening 122. To remove the prosthetic device 124, the wall 118 of the test chamber 102 may be removed from the mounting plate 308. The wall 118 may be removed from the mounting plate 308 by being rotated to unlock with the locking structure 315 and being slid axially away from the mounting plate 308. With the wall 118 removed from the mounting plate 308, the securing ring 306 may be uncoupled from the locking structure 315 of the wall **31*o*. The prosthetic device 124 may accordingly be removed from the retainer 302. A different prosthetic device 124 may then be coupled to the retainer 302** for testing.

The test chamber 102 may be configured for a particular type of prosthetic device. For example, the size and shape of the retainer 302 may be set for a particular size or shape of prosthetic device. The particular test chamber to be utilized may be determined based on the type of prosthetic device to be tested. In one embodiment, the test chamber 102 may have a different configuration than shown. For example, the size and shape of the test chamber may vary, or in one embodiment, the test chamber may not be separable from the remainder of the testing apparatus 100.

Figure 4:
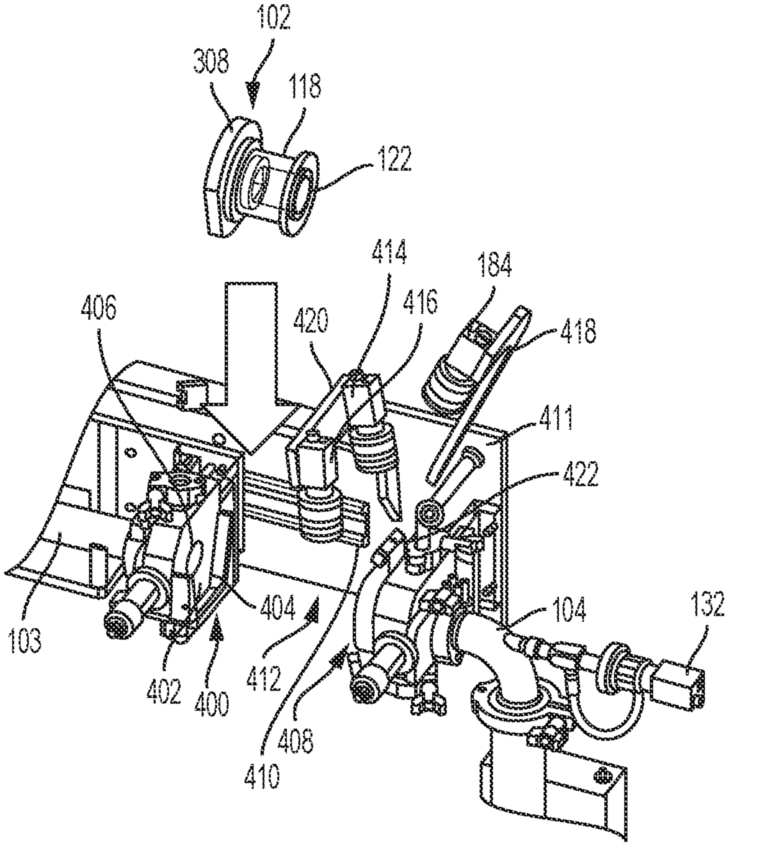
FIG. 4 illustrates a perspective view of a test chamber being inserted into a mount according to an embodiment of the present disclosure.

The test chamber 102 may comprise a unit for insertion into a mount of the testing apparatus 100. The wall 118, mounting plate 308, and retainer 302 (marked in FIG. 3), with the prosthetic device 124 positioned therein, may comprise a unit, as shown in FIG. 4. The mounting plate 308 may be locked to the wall 118 as discussed previously. The unit may be configured to be coupled to the mount, and may also be configured to be separable from the mount of the testing apparatus 100 and the fluid conduits 103, 104 of the testing apparatus 100.

FIG. 4 illustrates a perspective view of an implantation of the testing apparatus 100 in an opened configuration. The testing apparatus 100 in the opened configuration may have a portion open to allow for coupling of the test chamber 102 to the fluid conduits 103, 104. The testing apparatus 100 in the opened configuration may include a gap 412 positioned between a mount 400 and a mount 408 to accommodate the test chamber 102. The fluid conduits 103, 104 in FIG. 4 are shown to be separated from each other in the opened configuration to allow for insertion of the test chamber 102 therebetween. The test chamber 102 is shown being inserted into the mount 400 of the testing apparatus for coupling to the conduit 103.

The mount 400 may be positioned at an end portion of the conduit 103. The mount 400 may be configured to couple with the test chamber 102 and couple the test chamber 102 to the fluid conduit 103. The mount 400 may include a mount surface 402 and a receiver 404 for receiving the test chamber 102. The mount surface 402 may comprise a surface for contacting the mounting plate 308 when the test chamber 102 is inserted into the mount 400. The mount surface 402 may include an opening 406 for passing fluid through the opening 120 of the mounting plate 308 when the test chamber 102 is inserted into the mount 400 of the testing apparatus.

The receiver 404 may comprise a slot for receiving the test chamber 102. The mounting plate 308 of the test chamber 102 may slide into the slot to couple the test chamber 102 to the receiver 404 and accordingly couple the test chamber 102 to the fluid conduit 103.

Figure 10:
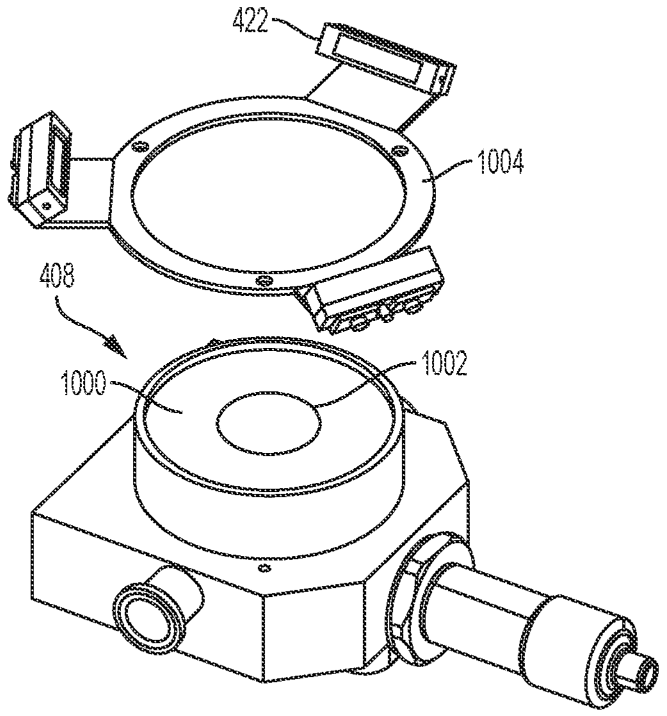
FIG. 10 illustrates an expanded perspective view of lights and a mount according to an embodiment of the present disclosure.

The mount 408 may be positioned at the opposite end of the test chamber 102 from the mount 400. The mount 408 may be positioned at an end portion of the conduit 104. The mount 408 is more clearly shown in FIG. 10 in a front perspective view. Referring to FIG. 10, the mount 408 may include a mount surface moo and an opening 1002. The mount surface moo may be configured to press against the wall 118 of the test chamber 102 and seal with the seal 316 of the wall 118. The opening 1002 may be configured to pass fluid through the opening 122 of the wall 118.

Referring back to FIG. 4, the mount 400, fluid conduit 103, and test chamber 102 may be configured to slide relative to the fluid conduit 104 and the mount 408. The test chamber 102, when coupled to the mount 400, may be configured to slide towards the mount 408 to seal with the mount surface woo of the mount 408 and move the testing apparatus 100 to a closed configuration. The mount 400, fluid conduit 103, and test chamber 102 may be configured to slide along a slide structure such as a rail 410 towards the mount 408. The rail 410 may be coupled to a support structure 411 of the testing apparatus 100, such that the mount 400, fluid conduit 103, and test chamber 102 may move relative to the support structure 411 along the rail 410.

Figure 5:
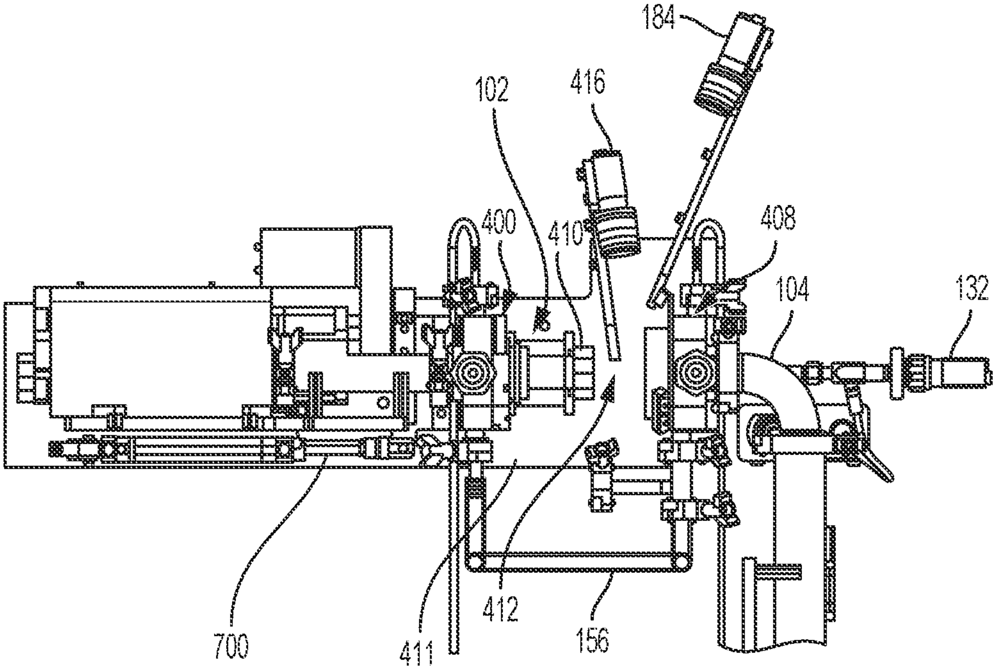
FIG. 5 illustrates a side view of a test chamber inserted into a mount according to an embodiment of the present disclosure.

FIG. 5 illustrates a side view of the testing apparatus 100 in the opened configuration, with the test chamber 102 coupled to the mount 400. The mount 400 and test chamber 102 are positioned away from the mount 408 with a gap 412 between the test chamber 102 and the mount 408.

Figure 6:
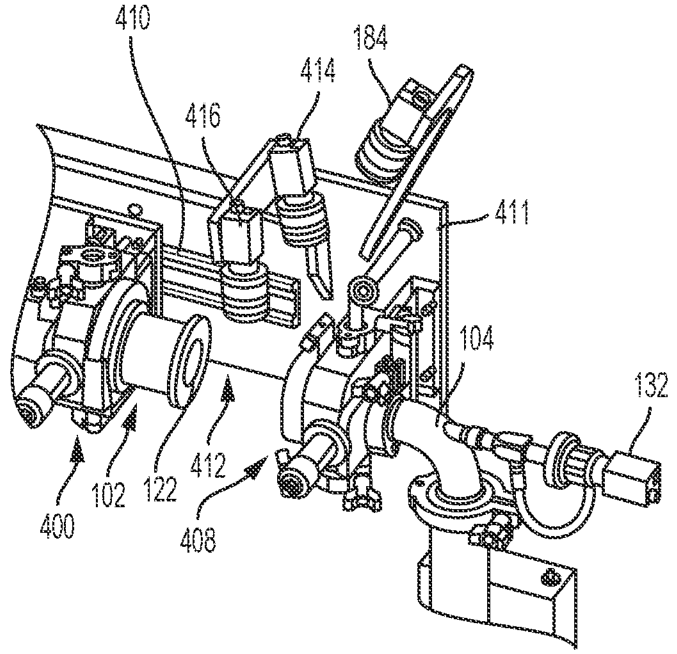
FIG. 6 illustrates a perspective view of a test chamber inserted into a mount according to an embodiment of the present disclosure.

FIG. 6 illustrates a perspective view of the test chamber 102 coupled to the mount 400 with the testing apparatus 100 in the opened configuration.

Upon the test chamber 102 being coupled to the mount 400, the test chamber 102, fluid conduit 103, and mount 400 may be slid towards the mount 408 along the rail 410.

Figure 7:
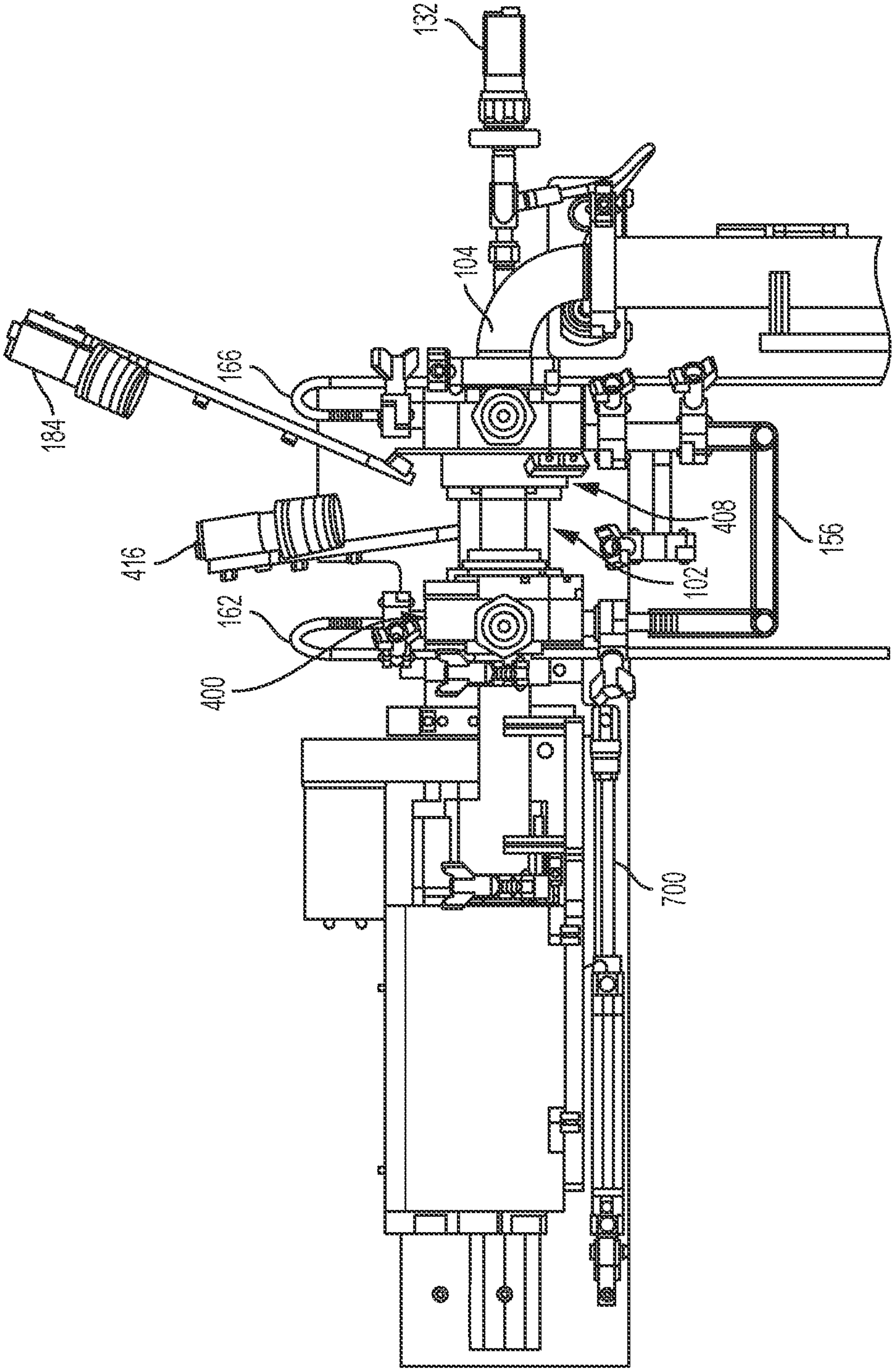
FIG. 7 illustrates a side view of a test chamber inserted into a mount according to an embodiment of the present disclosure.

FIG. 7 illustrates a side view of the test chamber 102 having been slid towards the mount 408 and in position for testing. The testing apparatus 100 is in a closed configuration, with the gap 412 having been closed. A piston 700 or other actuator device for moving the mount 400, fluid conduit 103, and test chamber 102 to the mount 408 may be utilized. The test chamber 102 may seal with the mount surface moo of the mount 408 via the force of the piston 700 driving the test chamber 102 towards the mount surface woo and pressing the test chamber 102 against the mount surface moo.

Upon the mount 400, fluid conduit 103, and test chamber 102 being slid towards the mount 408, the flow channel 105 may be filled with test fluid. Referring to FIG. 1, the flow channel 105 may be filled in a process in which the fluid drivers 106, 108 are both initially retracted in a direction away from the test chamber 102. A storage portion 131 of the fluid conduit 104 adjacent the fluid driver 108 may be filled with test fluid. The test fluid may have already been present in the flow channel 105 due to prior testing operations, and the retracted movement of the fluid driver 108 may allow the test fluid to drain from the horizontal portion of the flow channel 105 and be stored vertically in the storage portion 131. The fluid driver 108 may then be moved in a direction towards the test chamber 102 to push the test fluid through a test fluid return channel 156 to reach the opposite or upstream or inflow side of test chamber 102 with a valve 158 of the test fluid return channel 156 remaining open.

Purge channels 162, 166 may then be utilized with purge valves 164, 168 open to fill and pressurize the flow channel 105 with test fluid. The test fluid may fill the flow channel 105 until a desired pressure of the test fluid is provided in the flow channel 105. The flow channel 105 may be filled with test fluid until fluid sensors 178, 180 detect a continuous flow of fluid along the purge channels 162, 166 without air bubbles. Upon the fluid sensors 178, 180 detecting a continuous flow of fluid, the purge valves 164, 168 may be closed and pressure across the prosthetic device 124 may be allowed to equalize through the test fluid return channel 156. The valve 158 may then be closed to allow for a testing operation of the prosthetic device 124.

Upon a desired testing operation being performed or completed for the prosthetic device 124, the purge valves 164, 168 may be opened to allow air to enter the flow channel 105 and the second fluid driver 108 may move to a retracted position away from the test chamber 102 to store the test fluid within the adjacent storage portion 131 of the fluid conduit 104 and withdraw the test fluid from the remaining portion of the flow channel 105. Upon the test fluid being withdrawn from the test chamber 102, the test chamber 102, mount 400, and fluid conduit 103 may be slid away from the mount 408 with the testing apparatus wo moving to the opened configuration as shown in FIGS. 5 and 6. The test chamber 102 may then be removed from the receiver 404 shown in FIG. 4, and the prosthetic device 124 may be removed from the test chamber 102. A different prosthetic device may be inserted into the test chamber 102 for testing, or a different test chamber 102 may be utilized, and the process may start again. In one embodiment, the test fluid may be drained entirely from the flow channel 105 via the purge channels 162, 166 or another conduit or valve.

Referring to FIG. 1, the fluid conduits 103, 104 may define a flow channel 105 having a first end portion 126 and a second end portion 128. A portion 130 of the flow channel 105 may be bent to allow a camera 132 to have an axial view of the prosthetic device 124 without the fluid driver 108 impeding the view of the prosthetic device 124. The portion 130 of the flow channel may bend to form a vertical portion that serves as the storage portion 131 of the test fluid when the testing is completed or not occurring. The vertical orientation of the storage portion 131 may allow the portion 131 to retain the test fluid without the test fluid passing through the remaining horizontal portion of the flow channel 105 or the test chamber 102. In other embodiments, the flow channel 105 may have different configurations. For example, the entirety of the flow channel 105 may have a straightened configuration, or in one embodiment the entirety of the flow channel 105 may be configured to be positioned vertically, among other configurations.

The flow channel 105 may be configured to hold the test fluid and have the test fluid flow through the flow channel 105 from the first end portion 126 to the second end portion 128. The flow channel 105 may allow for fluid flow through the prosthetic device 124 and the internal cavity 300 of the test chamber 102. The flow channel 105 may be configured to be sealed in use, such that a defined amount of test fluid may be present in the flow channel 105 during use of the testing apparatus 100. Preferably, the flow channel 105 is entirely filled with test fluid between the fluid drivers 106, 108 during use of the testing apparatus 100. The flow channel 105 preferably has a static volume, such that no compliant or other flexible portions of the flow channel 105 allow the volume of the flow channel 105 to increase when the flow channel 105 is filled with test fluid. As discussed previously, the test fluid may be pressurized in the flow channel 105 such that the entire volume of the flow channel 105 is filled with test fluid and no air bubbles or a minimal number of air bubbles are present in the flow channel 105.

The first fluid driver 106 may be coupled to the first end portion 126 of the flow channel 105 and positioned at the first end portion 126 of the flow channel 105 and may include a piston 134, a motor 136, and a position sensor 138. The first fluid driver 106 may be configured to move to flow the test fluid through the prosthetic device 124 in an outflow direction (or downstream direction) of the prosthetic device 124, and may be configured to provide a pressure of the test fluid on an inflow side (or upstream side) of the prosthetic device 124. The piston 134 may be positioned in the fluid conduit 103 and configured to displace the test fluid via the volume of the piston and drive test fluid within the flow channel 105 by applying a force to the test fluid. The piston 134 may have a known geometry, such that a known displacement of the test fluid is provided based on the position of the piston 134 within the fluid conduit 103. The piston 134 may be sealed within the fluid conduit 103 to prevent the test fluid from exiting the fluid conduit 103. The piston 134 may have the configuration of a rod extending within the fluid conduit 103, with a seal of the fluid conduit 103 at the back end of the piston 134 to prevent the test fluid from exiting the back end of the fluid conduit 103. In such an embodiment, the volume of the piston 134 present within the fluid conduit 103 defines the displacement volume of the test fluid. In one embodiment, the piston 134 may have a configuration of a piston head and stem extending within the fluid conduit 103, as shown in FIG. 1.

The motor 136 may comprise a linear motor, or may comprise another form of motor as desired. The motor 136 may be configured to move the piston 134 and cause the piston 134 to apply a force to the test fluid. In embodiments, the motor 136 may have an accuracy to move the piston 134 on the order of microns. In other embodiments, other ranges of accuracy may be utilized.

The position sensor 138 may be configured to determine the position of the piston 134. The position sensor 138 may be utilized with the motor 136 to provide a reading of the position of the piston 134 upon the motor 136 moving the piston 134. In one embodiment, the position sensor 138 may comprise a drive encoder. The position sensor 138 may be configured to determine a speed of the movement of the piston 134 based on the readings of position.

In other embodiments, the first fluid driver 106 may have a different form, for example another form of fluid driver for displacing fluid may be utilized, such as a bellows or a diaphragm. In one embodiment, the first fluid driver 106 may comprise an impeller or the like if the displacement of the test fluid provided by the impeller may be determined.

The second fluid driver 108 may be coupled to the second end portion 128 of the flow channel 105 and positioned at the second end portion 128 of the flow channel 105. The second fluid driver 108 may include a piston 144, a motor 146, and a position sensor 148, which may each be configured similarly as the respective piston 134, motor 136, and position sensor 138 of the first fluid driver 106. The dimensions of the piston 144 may vary from the dimensions of the piston 134 in embodiments. The second fluid driver 108 may be configured to move to flow the test fluid through the prosthetic device 124 in the outflow direction (or downstream direction) of the prosthetic device 124 by being retracted in a direction away from the test chamber 102, and may be configured to provide a pressure of the test fluid on an outflow side (or downstream side) of the prosthetic device 124.

The first fluid driver 106 and the second fluid driver 108 may be positioned at opposite ends of the flow channel 105 and may be configured to apply a force to the test fluid in the flow channel 105 in opposite directions.

The first fluid driver 106 and the second fluid driver 108 may be configured to move in coordination with the respective other fluid driver 108, 106. The test fluid may be incompressible, and as such, the second fluid driver 108 must move to allow a flow of the test fluid through the prosthetic device 124 upon movement of the first fluid driver 106. The second fluid driver 108 may move to displace an equal and opposite amount of test fluid within the flow channel 105 to allow for fluid flow through the prosthetic device 124. A possible variation in the dimensions of the pistons 134, 144 may be accounted for to allow for an equal and opposite displacement of test fluid within the flow channel 105.

In an embodiment in which test fluid flows through the prosthetic device 124 in the rightward direction (as shown in FIG. 1), the first fluid driver 106 may be considered to be positioned on the upstream or inflow side of the prosthetic device 124 and the second fluid driver 108 may be considered to be positioned on the downstream or outflow side of the prosthetic device 124. The first fluid driver 106 may drive test fluid through the prosthetic device 124 in the rightward direction until all the test fluid passes through the prosthetic device 124, or until the desired testing operation has occurred or completed. The testing apparatus 100 may accordingly utilize the test fluid return channel 156 to pass test fluid back to the upstream side of the prosthetic device 124. The test fluid return channel 156 may include a valve 158 to allow or prevent fluid flow through the test fluid return channel 156. The test fluid return channel 156 may include a flow restrictor 160 to set a desired amount of return flow to the upstream side of the prosthetic device 124. The valve 158 may remain closed during testing of the prosthetic device 124. As discussed, the test fluid return channel 156 may also be utilized in a filling process of the flow channel 105 with test fluid, to equalize pressure on both sides of the prosthetic device 124.

The first pressure sensor 110 may be configured to determine a pressure of the test fluid between the first fluid driver 106 and the prosthetic device 124 within the flow channel 105. The second pressure sensor 112 may be configured to determine a pressure of the test fluid between the second fluid driver 108 and the prosthetic device 124 within the flow channel 105. In an embodiment in which test fluid flows through the prosthetic device 124 in the rightward direction (as shown in FIG. 1), the first pressure sensor 110 may be considered to determine a pressure of the test fluid on the upstream or inflow side of the prosthetic device 124 and the second pressure sensor 112 may be considered to determine a pressure of the test fluid on the downstream or outflow side of the prosthetic device 124.

The testing apparatus 100 may include a purge channel 162 configured to fill and purge test fluid in the flow channel 105 between the first fluid driver 106 and the prosthetic device 124. A valve 164 may be configured to control flow through the purge channel 162. A purge channel 166 may be configured to fill and purge test fluid in the flow channel 105 between the second fluid driver 108 and the prosthetic device 124. A valve 168 may be configured to control flow through the purge channel 166. The testing apparatus 100 may include a back pressure accumulator 170 and a back pressure relief valve 172 to reduce excessive fluid pressure in the flow channel 105. As discussed, the purge channels 162, 166 may be utilized to fill the flow channel 105 with a desired amount of test fluid, and may be utilized to evacuate air bubbles from the flow channel 105.

The testing apparatus 100 may include a catch basin 174 and a fluid container 176 for receiving fluid from the flow channel 105. The fluid may fall to the fluid container 176 upon the test chamber 102 being slid or retracted from the mount 408.

The testing apparatus 100 may include a fluid sensor 178 configured to determine the presence of fluid in the flow channel 105 between the first fluid driver 106 and the prosthetic device 124. The testing apparatus 100 may include a fluid sensor 180 configured to determine the presence of fluid in the flow channel 105 between the second fluid driver 108 and the prosthetic device 124. In one embodiment, the fluid sensors 178, 180 may be positioned in line with the respective purge channels 162, 166 before the respective valves 164, 168. As discussed, the fluid sensors 178, 180 may be utilized to determine when the flow channel 105 is entirely filled with test fluid and the air within the flow channel 105 has been removed.

Figure 9:
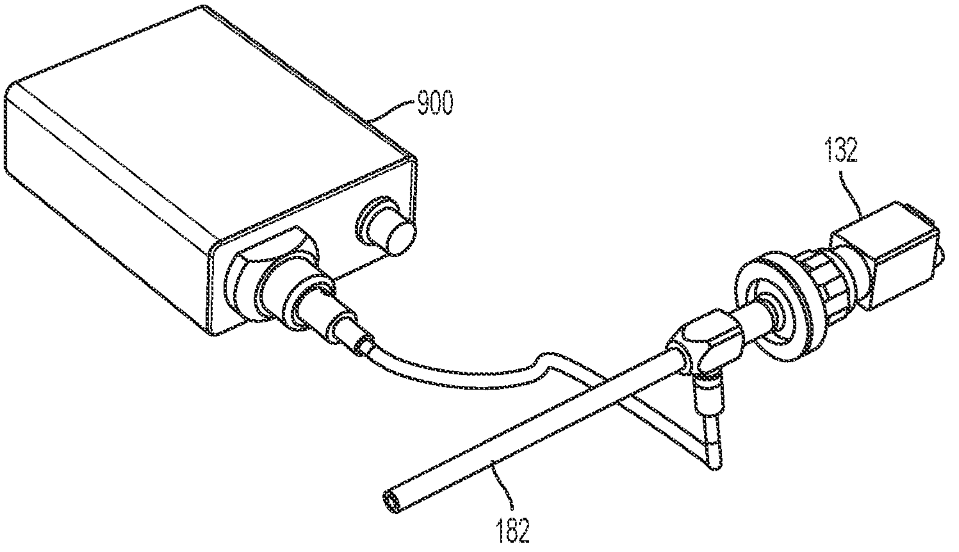
FIG. 9 illustrates a perspective view of a camera and an endoscope according to an embodiment of the present disclosure.

The testing apparatus 100 may include a camera system for viewing the prosthetic device 124 within the test chamber 102. The camera system may include an axial camera 132 for viewing the prosthetic device 124 along its axis or the axis of the flow channel 105. The axial camera 132 may be coupled to an endoscope 182. The endoscope 182 may pass through the outer surface of the fluid conduit 104 and may be positioned within the flow channel 105. The endoscope may allow the axial camera 132 to view within the flow channel 105 and may include one or more lights for lighting the view of the axial camera 132. FIG. 9 illustrates a perspective view of the axial camera 132 and endoscope 182. The axial camera 132 may couple to a camera controller 900 that may be configured to provide power and controls to the axial camera 132 and may provide the lighting for the endoscope 182.

Referring back to FIG. 1, the camera system may include one or more side cameras 184 for viewing a side of the prosthetic device 124. The one or more side cameras 184 may be positioned on a side of the test chamber 102. FIG. 4 illustrates the position of side camera 184, as well as side cameras 414, 416. The side cameras 184, 414, 416 may be fixed to one or more camera mounts 418, 420. The camera mounts 418, 420 may be fixed in position, or may be configured to move axially or radially relative to the test chamber 102. In the embodiment shown in FIG. 4, one or more of the side cameras 184, 414, 416 may view the prosthetic device via mirrors positioned around the test chamber 102.

The camera system may include one or more lights 422. The one or more lights 422 may be configured to be positioned around the test chamber 102 and may be configured to shine light upon the prosthetic device 124. FIG. 10, for example, illustrates a perspective view of the lights 422 coupled to a ring 1004 for positioning around the test chamber 102. The ring 1004 may be positioned around the mount surface moo of the mount 408 with the lights 422 angled to shine towards the prosthetic device 124.

FIG. 2 illustrates a perspective view of an implementation of the testing apparatus 100. The support structure 200 may retain the components of the testing apparatus 100 in position, and may include a frame for retaining the components of the testing apparatus 100. The support structure 200 may include a working surface 204 for a user to utilize when operating the testing apparatus 100. The support structure 200 may include wheels 206 such that the testing apparatus 100 is movable and portable if desired.

The control terminal 202 may include a display screen 208 and an input terminal 210. The display screen 208 may display features of operation of the testing apparatus 100 and properties of the prosthetic device 124, and may be configured for a user to utilize to provide input to the testing apparatus 100 (via a touchscreen or the like). The input terminal 210 may comprise a keyboard or other input terminal for a user to utilize to provide input to the testing apparatus 100.

Figure 8:
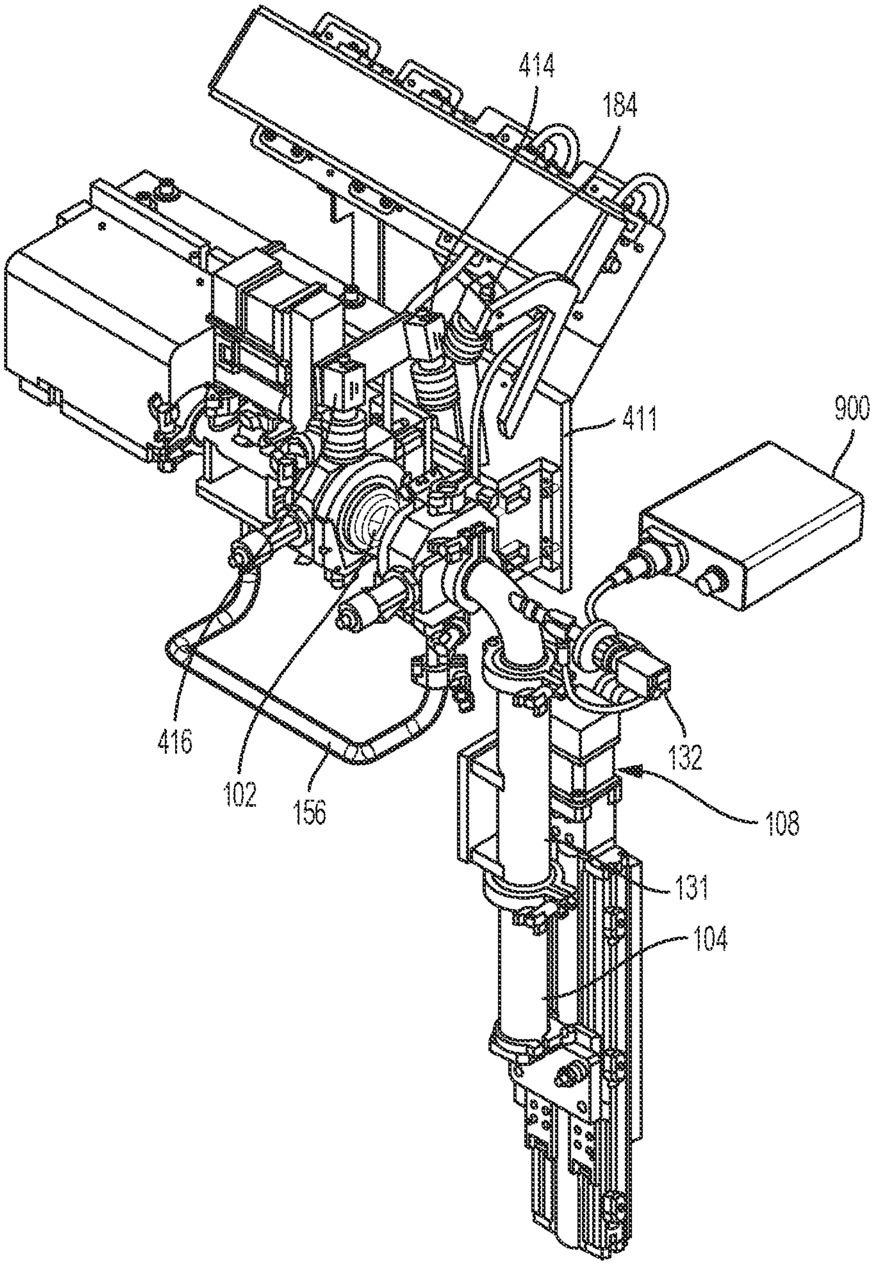
FIG. 8 illustrates a perspective view of a portion of a testing apparatus according to an embodiment of the present disclosure.

FIG. 8 illustrates a perspective view of an implementation of a portion of the testing apparatus 100.

Figure 11:
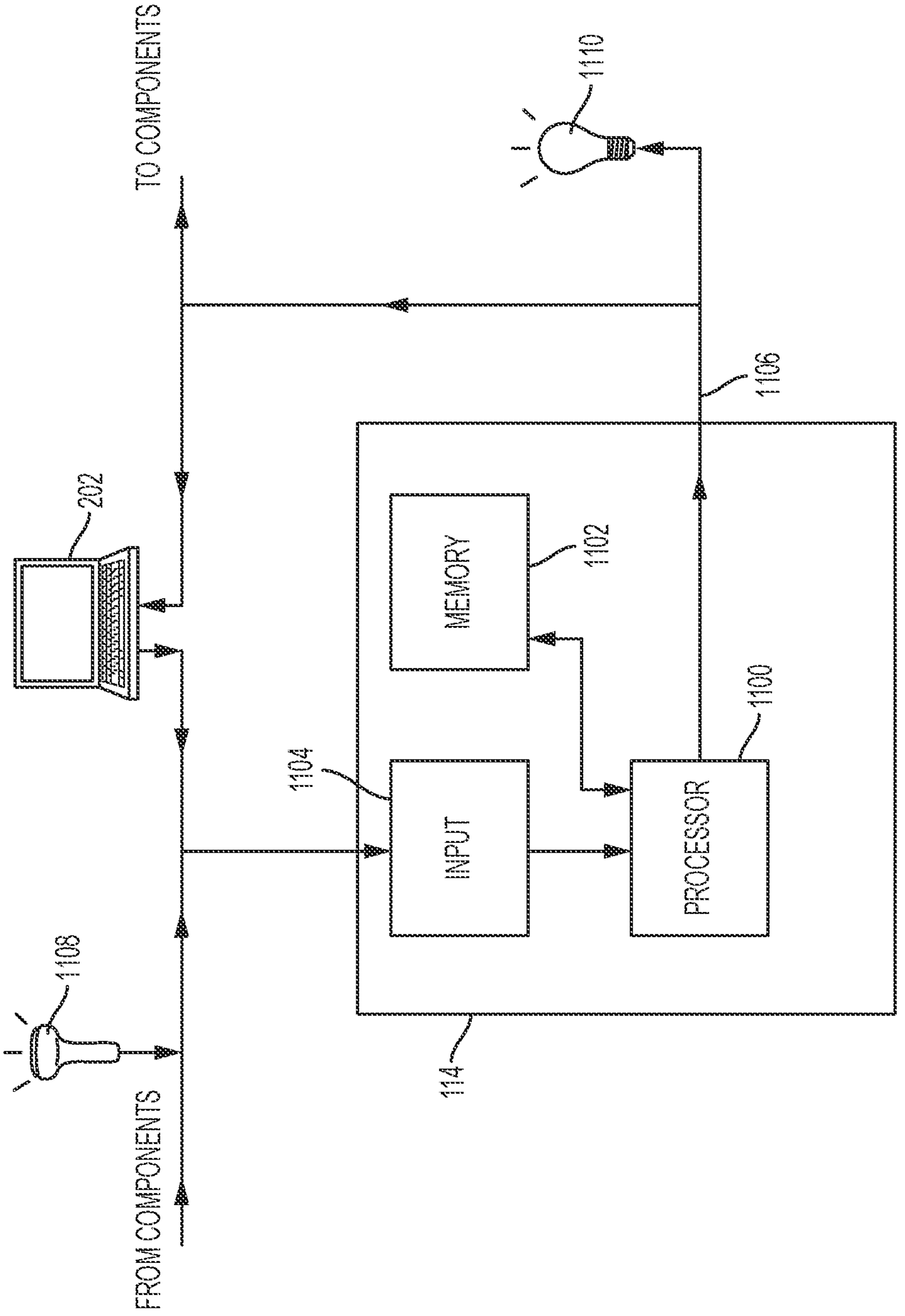
FIG. 11 illustrates a schematic view of a controller and components according to an embodiment of the present disclosure.

FIG. 11 illustrates a schematic view of the controller 114. The controller 114 may be utilized to control the operation of the testing apparatus 100 and may be utilized to process and provide an output of the operation of the testing apparatus 100. For example, the controller 114 may be configured to move the first fluid driver 106 and the second fluid driver 108 to flow the test fluid through the prosthetic device 124 in the outflow direction (or downstream direction) of the prosthetic device 124 when the prosthetic device 124 is in an open state. The controller 114 may be configured to operate the first fluid driver 106 to provide a pressure profile of the test fluid on the inflow side (or upstream side) of the prosthetic device 124 when the prosthetic device 124 is in a closed state. The controller 114 may be configured to operate the second fluid driver 108 to provide a pressure profile of the test fluid on the outflow side (or downstream side) of the prosthetic device 124 when the prosthetic device 124 is in a closed state. The controller 114 may be configured to move the first fluid driver 106 and the second fluid driver 108 to provide pulsatile flow through the prosthetic device 124. The controller 114 may provide other operations of the testing apparatus 100.

Referring to FIG. 11, the controller 114 may include a processor 1100, a memory 1102, an input 1104, and an output 1106. The processor 1100 may comprise one or more microprocessors, or may comprise another form of processor as desired. The processor 1100 may be configured to process and execute the operations of the controller 114 and the testing apparatus 100, and may be configured to process and provide an output of the operation of the testing apparatus 100. For example, the processor 1100 may be configured to execute the testing operations of the testing apparatus 100, including the operations of the fluid drivers 106, 108. The processor 1100 may be configured to operate the fluid drivers 106, 108 according to testing profiles of the testing apparatus 100, for example, according to the displacement models 1302, 1502, pressure models 1308, 1508, and one or more pressure targets 1318, 1518 represented in FIGS. 13 and 15. The processor 1100 may be configured to operate the fluid drivers 106, 108 according to the corrective adjustments 1322, 1522 represented in FIGS. 13 and 15. The processor 1100 may be configured to receive output signals from sensors, such as the position sensors 138, 148, and pressure sensors 110, 112 and process such signals and provide an output of a property of the prosthetic device being tested. The processor 1100 may be configured to operate the filling of test fluid within the flow channel 105, and may be configured to operate the movement of the testing apparatus 100 from the opened configuration to the closed configuration. In one embodiment, the processor 1100 may be configured to operate the camera system of the testing apparatus 100, including processing the images of the camera system and providing a determination of properties of the prosthetic device shown in the images, including the properties of leaflets of a prosthetic valve such as coaptation. Other processing operations may be provided by the processor, including the operations disclosed herein. In one embodiment, the processor may be positioned remotely from the testing apparatus 100 or may be configured in a network or cloud computing configuration, or in one embodiment may physically be within a controller body coupled to the testing apparatus 100.

The memory 1102 may be configured to store information for use by the processor 1100 and the testing apparatus 100. The memory 1102 may comprise a hard drive, RAM, ROM, or other form of memory. The memory 1102 may be configured to store non-transitory data therein. The memory 1102 may comprise a solid state memory or other form of memory. In one embodiment, the memory 1102 may be positioned remotely from the testing apparatus, and similar to the processor 1100, may be configured in a network or cloud computing configuration, or in one embodiment may physically be within a controller body coupled to the testing apparatus 100.

The information stored in the memory 1102 may include properties of the prosthetic device 124, and may include testing profiles for testing the prosthetic device 124. The testing profiles, for example, may include the displacement models 1302, 1502, pressure models 1308, 1508, or one or more pressure targets 1318, 1518 represented in FIGS. 13 and 15. The memory 1102 may also be configured to store the corrective adjustments 1322, 1522 represented in FIGS. 13 and 15. Other information, such as other parameters including feedback parameters, for operation of the testing apparatus 100 may be stored by the memory 1102. Testing profiles for operating the camera system and processing the images of the camera system may be stored in the memory 1102, including calibration scalings.

The information stored in the memory 1102 may be matched to the type of prosthetic device 124 being tested by the testing apparatus 100. For example, a particular type of prosthetic device 124 being tested may result in a particular testing profile being utilized by the testing apparatus 100. Multiple testing profiles or other parameters may be stored in the memory 1102, each corresponding to a type of prosthetic device 124. The processor 1100 may be configured to retrieve the testing profile or other parameters for testing a particular type of prosthetic device 124 being tested.

The input 1104 may be configured to receive an input from an input device. The input 1104 may comprise a variety of inputs, including an analog input, digital input, Ethernet input, among other forms of input. The input device may comprise the control terminal 202, or another form of input device such as a barcode scanner 1108 or input terminal 210. The input device may be utilized by a user to indicate an operation to be performed by the testing apparatus 100. For example, the barcode scanner 1108 may be utilized to scan a code corresponding to the prosthetic device 124 to be tested. The scanned code may indicate the type of prosthetic device 124 and may be utilized to retrieve the testing profile or other parameter for the particular type of prosthetic device 124 from the memory 1102. Such an input may also be provided at the control terminal 202. The input may also include a variation of the testing profile or other parameter to be provided. For example, a user may determine that a modification of a testing profile be provided, and may input that request to the controller 114 via the input 1104. The input may also be utilized for manual input of a testing cycle (for example, a start or finish of a testing cycle) and manual input of the type of the prosthetic device being tested, or manual input of other operations of the testing apparatus 100 (for example moving the testing apparatus 100 between opened and closed configurations).

The controller 114 may be configured to receive an input from any or all of the components of the testing apparatus 100, including the pressure sensors, the cameras, the fluid drivers, the position sensors, or the liquid sensors, among other components. The input may comprise a signal from any of the components. The controller 114 may be configured to process the signal provided from the components, for example, the controller 114 may be configured to determine a movement of the fluid drivers 106, 108 based on a signal from the respective position sensors 138, 148. The controller 114 may be configured to output a signal (which may include a control signal) to any or all of the components of the testing apparatus 100, including the pressure sensors, the cameras, the fluid drivers, the position sensors, or the liquid sensors, among other components. The controller 114 may also be configured to receive input and provide output regarding the filling of the flow channel 105. For example, the controller 114 may be configured to automatically fill the flow channel 105 and operate the piston 700 to move the testing apparatus between the opened configuration and the closed configuration.

The output 1106 may comprise a property of the prosthetic device 124, or a property of the testing of prosthetic device 124. The output 1106, for example, may indicate a property of the prosthetic device 124 being tested, such as effective orifice area (EOA) of the prosthetic device 124. Other testing results, such as other flow properties, may be provided by the output 1106. The output 1106 may output the results of processing performed by the controller 114. The output 1106 may indicate the testing of the prosthetic device 124, such as the current state of operation of the testing. The output 1106 may also be utilized to provide a signal (which may include a control signal) to any or all of the components of the testing apparatus 100, including the pressure sensors, the cameras, the fluid drivers, the position sensors, or the liquid sensors, among other components.

The output 1106 may be provided to the control terminal 202 for viewing by the user. In one embodiment, the output 1106 may be provided to another display screen as desired. In one embodiment, the output 1106 may be provided to an indicator 1110, which may include an indicator light or the like. The indicator 1110 may flash a certain color, or provide another form of display to indicate a property of the property of the prosthetic device 124, or a property of the testing of prosthetic device 124. For example, if the prosthetic device 124 is found to have passed the testing process, then a green light may illuminate, and if the prosthetic device 124 is found to have failed the testing process, then a red light may illuminate. The memory 1102 may store threshold values for the properties of the prosthetic device 124, and if the prosthetic device 124 is found to violate one or more of those threshold values, the control 144 may output an indication (via the indicator 1110 or the like) that one or more properties of the prosthetic device 124 have not been met.

The controller 114 may comprise an apparatus that is separate from the control terminal 202, or may comprise a portion of the control terminal 202. In one embodiment, the controller 114 may be positioned remotely for remote operation of the testing apparatus 100. Any component of the controller 114 may be positioned remotely as desired. The controller 114 may include dedicated components for performing the operations disclosed herein. For example, a dedicated image processor may be provided by the controller for processing the images of the prosthetic device. In other embodiments, the controller 114 may have a different configuration than shown in FIG. 11. The controller 114 may include a single controller or multiple controllers. For example, the controller 900 shown in FIG. 9 and controller 114 shown in FIG. 11 may be considered together to constitute a single controller.

Figure 12:
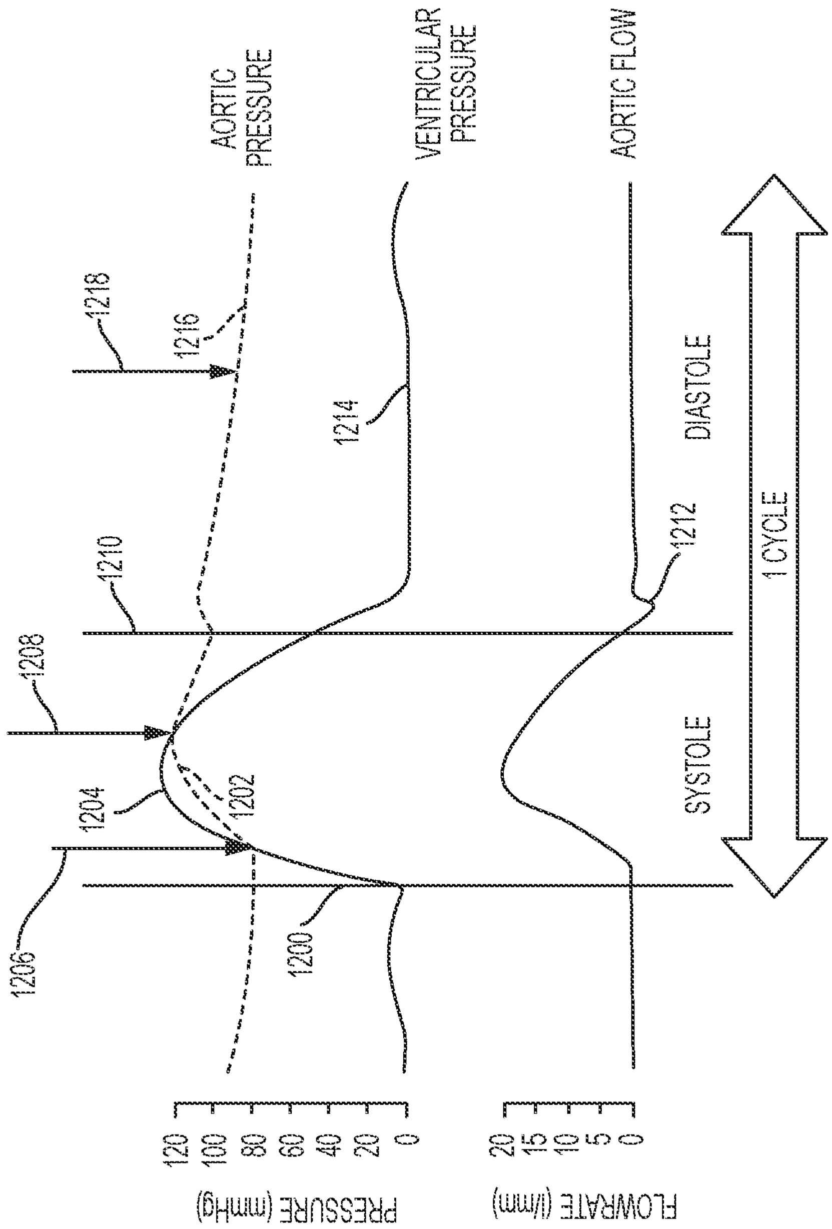
FIG. 12 illustrates a chart of an operation of a testing apparatus according to an embodiment of the present disclosure.

FIG. 12 illustrates a pressure and flow rate chart illustrating an operation of the testing apparatus 100 according to an embodiment of the present disclosure. The pressure and flow rate chart may be read in conjunction with the process chart shown in FIG. 13.

The testing apparatus 100 may be utilized to perform flow testing of prosthetic devices, and may be utilized to identify leakage of a prosthetic device. The testing apparatus 100 may be utilized to test prosthetic valves. The valves may be tested under pulsatile conditions that may mimic physiological conditions. The valves may comprise prosthetic heart valves, and the physiological conditions may mimic the operation of a heart.

The testing apparatus 100 may be configured to produce systolic and diastolic conditions to provide measurements of properties of the prosthetic heart valve. Such properties may include flow properties such as effective orifice area (EOA), and may include a measurement of the coaptation of the valve leaflets. Such properties may include an identification of leakage of the valve and a determination of the amount of leakage, and may include an average and/or standard deviation of any of the properties of the valve. A pressure gradient of the valve may be determined, and other hydrodynamic measurements of the valve may be provided.

The testing apparatus 100 may be configured to perform flow testing of prosthetic aortic heart valves, and may be utilized to identify and determine an amount of leakage of a prosthetic aortic heart valve. Testing of prosthetic aortic heart valves is disclosed in regard to FIGS. 12 and 13. The pulsatile conditions may mimic the physiological conditions applied to an aortic heart valve in the human heart.

The testing apparatus 100 may operate the fluid drivers 106, 108 to pass fluid through the prosthetic aortic heart valve, which may be positioned within the testing apparatus 100 in a similar manner as the prosthetic device 124. The controller 114 marked in FIG. 1 may be utilized to operate the testing apparatus 100 and provide the process shown in FIGS. 12 and 13 and resulting outputs. The processor of the controller 114, or other components of the controller may be utilized to operate the testing apparatus 100 and provide the process shown in FIGS. 12 and 13 and resulting outputs, and may utilize a software method or other method to operate the testing apparatus 100 and provide the process shown in FIGS. 12 and 13 and resulting outputs.

The prosthetic aortic heart valve may be configured to pass fluid from the upstream position (or inflow side) discussed in regard to FIG. 1 to the downstream position (or outflow side).

Under testing of the prosthetic aortic heart valve, the first fluid driver 106 may be considered a ventricular fluid driver, and the second fluid driver 108 may be considered an aortic fluid driver. The first pressure sensor 110 may be configured to determine the ventricular pressure (or pressure on the inflow side), and the second pressure sensor 112 may be configured to determine the aortic pressure (or pressure on the outflow side).

The testing apparatus 100 may operate as follows. Referring to FIG. 12, a start (indicated by line 1200) of a systole phase may initiate a rise in pressure on the ventricular side of the prosthetic aortic heart valve. During all of the systole phase of operation, the aortic heart valve may be in an opened state, with the valve opened to pass test fluid therethrough in the outflow direction.

Figure 13:
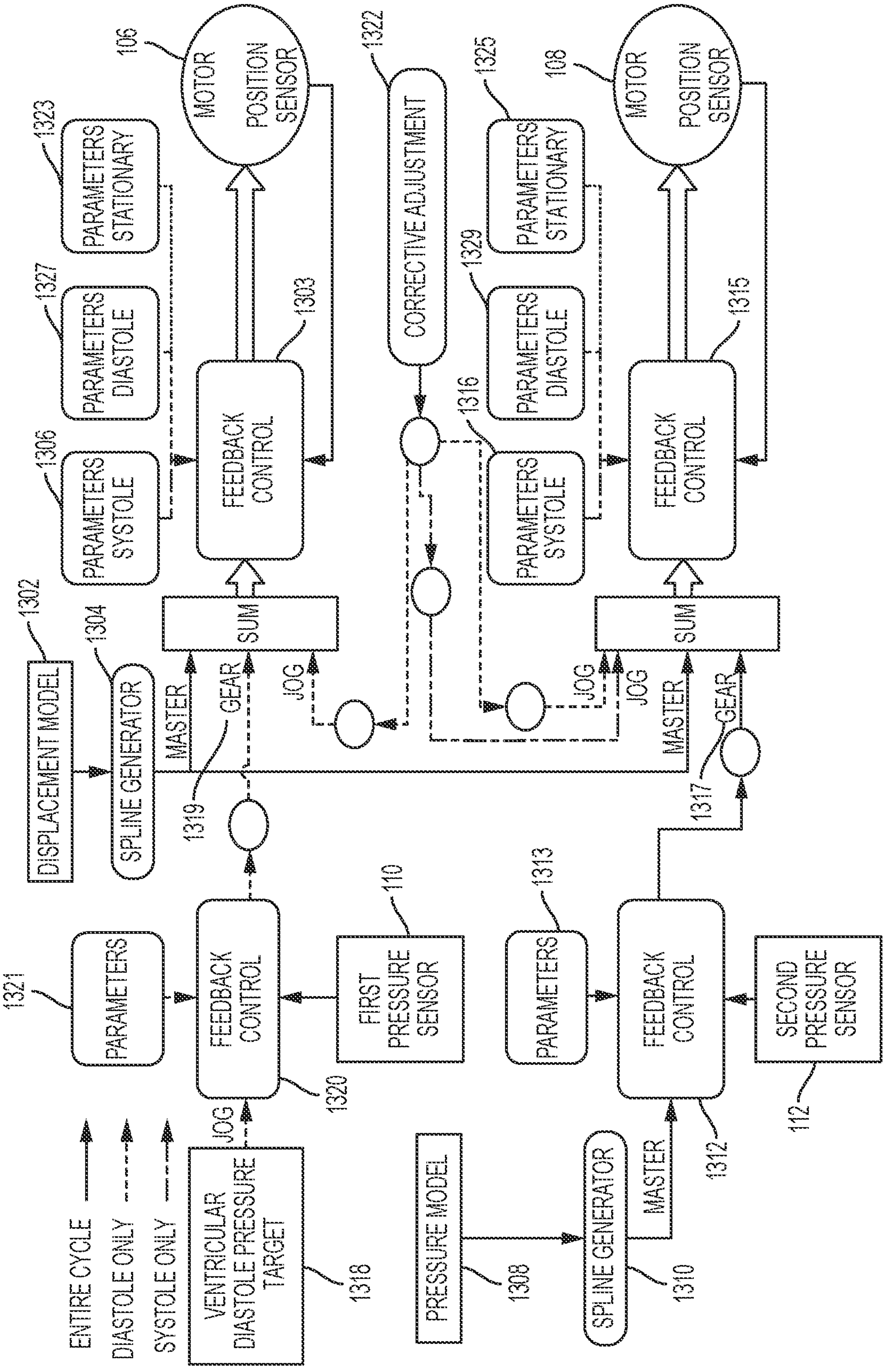
FIG. 13 illustrates a chart of an operation of a testing apparatus according to an embodiment of the present disclosure.

Referring to FIG. 13, the operation under the systole phase may start with a displacement model 1302 being provided to the first fluid driver 106 (the ventricular fluid driver) and to the second fluid driver 108 (the aortic fluid driver). The displacement model 1302 may be smoothed by a spline generator 1304 prior to being received by the first fluid driver 106 and the second fluid driver 108. The displacement model 1302 may indicate a prescribed movement for the first fluid driver 106 and for the second fluid driver 108. The first fluid driver 106 (the ventricular fluid driver) may operate based on the displacement model 1302. As such, the first fluid driver 106 follows a prescribed movement of position and speed based on the displacement model 1302. The displacement model 1302 may indicate the amount of displacement of the first fluid driver 106 (for example, the displacement of the piston 134 of the first fluid driver) as well as the timing of the displacement (for example, the speed at which the piston 134 moves). A feedback control 1303 may be provided to the first fluid driver 106 based on feedback from the position sensor 138 of the first fluid driver 106. The position sensor 138 may be configured to provide the position and movement (e.g., speed of movement) of the first fluid driver 106 (including the piston 134 of the first fluid driver).

During the systole phase, the feedback control 1303 may utilize feedback parameters 1306 that are configured for use by the feedback control 1303 during the systole phase. The feedback parameters 1306 may be utilized by the feedback control 1303 to indicate whether the first fluid driver 106 is following the prescribed displacement model 1302 and to provide feedback to allow the first fluid driver 106 to follow the displacement model 1302. The feedback control 1303 may comprise a PID control and the feedback parameters 1306 may comprise PID parameters.

During the systole phase, the pressure on the upstream or inflow side of the valve may be determined via the first pressure sensor no. However, feedback from the first pressure sensor 110 is not provided to the first fluid driver 106 during the systole phase, and the first fluid driver 106 may not operate based on a pressure model or one or more pressure targets during the systole phase. Rather, the first fluid driver 106 operates to provide flow through the prosthetic aortic heart valve in the outflow direction. The pressure profile 1204 shown in FIG. 12 may remain an artifact of the prescribed movement of the first fluid driver 106.

Referring to FIG. 13, the second fluid driver 108 (the aortic fluid driver) under the systole phase may receive the input from the displacement model 1302. The second fluid driver 108 may be configured to follow the displacement model 1302 to allow for a desired flow through the prosthetic aortic heart valve.

The second fluid driver 108, however, may also receive input from a pressure model 1308. The controller 114 accordingly is configured to move the second fluid driver 108 based on a pressure model 1308 when the prosthetic aortic heart valve is in an open state. The input from the pressure model 1308 may be smoothed by a spline generator 1310. The pressure model 1308 may comprise one or more pressures to be provided by the second fluid driver 108. The pressure may be provided by the second fluid driver 108 moving out of sync (asynchronously) with the first fluid driver 106 to cause the second fluid driver 108 to apply a pressure to the test fluid. Referring to FIG. 12, the pressure model 1308 may define a pressure profile 1202 (shown in dashed lines) for the second fluid driver 108 to provide on the aortic side (or outflow side) of the prosthetic aortic heart valve during the systole phase. The pressure profile 1202 may comprise a back pressure to be provided by the second fluid driver 108 during the systole phase, and may mimic a physiological back pressure profile provided by the human heart during the systole phase. The controller 114 may be configured to operate the second fluid driver 108 to provide a back pressure profile of the test fluid on the outflow side of the prosthetic aortic heart valve when the aortic heart valve is in the open state.

The input from the smoothed pressure model 1308 may be provided to a feedback control 1312. The feedback control 1312 may receive input from the second pressure sensor 112. The input from the second pressure sensor 112 may be provided to the feedback control 1312 to allow for feedback regarding the pressure on the aortic side (or outflow side) of the aortic heart valve. The feedback control 1312 may utilize feedback parameters 1313 that are configured for use by the feedback control 1312. The feedback control 1312 may comprise a PID control and the feedback parameters 1313 may comprise PID parameters.

The feedback from the second pressure sensor 112 may be utilized to allow the second fluid driver 108 to provide the desired pressure profile 1202 on the aortic side (or outflow side) of the aortic heart valve, and control the movement of the second fluid driver 108 to provide the desired pressure profile 1202. The second fluid driver 108 may move asynchronously with the first fluid driver 106 to provide the pressure profile 1202.

The output of the feedback control 1312 may be combined with the prescribed movement of the displacement model 1302 and input to a feedback control 1315 of the second fluid driver 108. A scaling factor 1317 may be utilized to set the proportionate value of the feedback control 1312 compared to the value provided by the displacement model 1302. These combined parameters may be provided to the feedback control 1315 of the second fluid driver 108.

The second fluid driver 108 may operate based on the displacement model 1302. The displacement model 1302 may indicate the displacement of the second fluid driver 108 (for example, the displacement of the piston 144 of the second fluid driver). The position sensor 148 may be configured to provide the position and movement (e.g., speed of movement) of the second fluid driver 108 (including the piston 144 of the second fluid driver). The second fluid driver 108 may be configured to provide an opposite and equal displacement of the test fluid to allow the test fluid to flow through the prosthetic aortic heart valve in a prescribed manner (although in an asynchronous manner to allow for the back pressure of the second fluid driver 108 based on the input from the feedback control 1312). The opposite and equal displacement results because the flow channel 105 is entirely filled with test fluid, and to allow for a flow of fluid, an equal and opposite amount of displacement by the second fluid driver 108 must be provided.

The feedback control 1315 may be provided to the second fluid driver 108 based on feedback from the position sensor 148 of the second fluid driver 108. During the systole phase, the feedback control 1315 may utilize feedback parameters 1316 that are configured for use by the feedback control 1315 during the systole phase. The feedback control 1315 may comprise a PID control and the feedback parameters 1316 may comprise PID parameters. The second fluid driver 108 accordingly may move based on the displacement model 1302 to provide a desired flow through the valve and may move based on a pressure model 1308 to provide a desired back pressure to the test fluid of the valve, with feedback provided by the pressure sensor 112.

A corrective adjustment 1322 may be provided to the second fluid driver 108 during the systole phase to allow the second fluid driver 108 to adjust its movement to provide a desired back pressure to the test fluid. The corrective adjustment 1322 may comprise an additional control that is provided to the second fluid driver 108 to account for a non-linear response of the pressure on the downstream or outflow side of the aortic heart valve to the movement of the second fluid driver 108. As such, the feedback controls 1315, 1312 may be unable to account for the non-linear response of the pressure on the downstream or outflow side of the valve to the movement of the second fluid driver 108 and the corrective adjustment 1322 may be utilized to provide the desired back pressure.

Referring to FIG. 12, upon operation of the first fluid driver 106 and the second fluid driver 108 during the systole phase, the first pressure sensor 110 may be configured to measure the pressure of the test fluid on the ventricular side (inflow side) of the prosthetic aortic heart valve, and the second pressure sensor 112 may be configured to measure the pressure of the test fluid on aortic side (outflow side) of the prosthetic aortic heart valve. A pressure gradient may be determined between the measured ventricular pressure on the inflow side (measured by the first pressure sensor no) and the measured aortic pressure on the outflow side (measured by the second pressure sensor 112) during the entire positive differential pressure period of the measured ventricular pressure and the measured aortic pressure, as marked between arrows 1206 and 1208. The controller 114 may be configured to determine, based on measurements of the first pressure sensor 110 and the second pressure sensor 112, a pressure differential between the test fluid on the inflow side and the test fluid on the outflow side of the prosthetic aortic heart valve when the prosthetic aortic heart valve is in an open state.

The controller 114 may be configured to determine, based on the measurements of the first pressure sensor 110 and the second pressure sensor 112, the time period (as shown between arrows 1206 and 1208) in which the pressure of the test fluid on the inflow side is greater than the pressure of the test fluid on the outflow side.

The measured pressure gradient may be utilized in the following equation to determine a property of the prosthetic aortic heart valve comprising the effective orifice area (EOA) of the prosthetic aortic heart valve:

$$EOA = \frac{q_{V_{RMS}}}{51.6\sqrt{\frac{\Delta p}{\rho}}}$$

In which:

EOA is the Effective Orifice Area (in $cm^2$);

$q_{V_{RMS}}$ is the root mean square forward flow (in mL/s) during the positive differential pressure period;

$\Delta p$ is the mean pressure difference (measured during the positive differential pressure period, in millimeters mercury (mmHg)); and $\rho$ is the density of the test fluid (which may be in $g/cm^3$).

The factor $q_{V_{RMS}}$ may be determined by the equation:

$$q_{V_{RMS}} = \sqrt{\frac{\int_{t_1}^{t_2} q_V(t)^2 dt}{t_2 - t_1}}$$

In which:

$q_{V_{RMS}}$ is root mean square forward flow during the positive differential pressure period;

$q_V(t)$ is instantaneous flow at time (t);

$t_1$ is time at start of positive differential pressure period (marked as line 1206); and $t_2$ is time at end of positive differential pressure period (marked as line 1208).

The controller 114 may be configured to determine the effective orifice area (EOA) of the prosthetic aortic heart valve based on the flow through the valve and based on the pressure differential between the test fluid on the inflow side and the test fluid on the outflow side of the aortic valve during the positive pressure period.

The flow through the aortic valve may be known based on the movement of the first fluid driver 106 and the second fluid driver 108. For example, the geometry of the pistons 134, 144 may be known such that the displacement of the pistons 134, 144 provided by the position sensors 138, 148 is used to determine the flow through the aortic valve. No flow meters or other flow sensors are utilized in such a method.

The measurement of effective orifice area (EOA) may be provided as an output upon the first instance of the systole phase occurring for the aortic heart valve, or, upon multiple instances of the systole phase occurring or being measured for the aortic heart valve. For example, multiple cycles of the systole phase and diastole phase may occur before the measure of effective orifice area is provided. The measurement of effective orifice area (EOA) may be provided as a quantitative value, and may include an average and/or standard deviation value for the aortic heart valve.

At the conclusion of the systole phase, the testing apparatus 100 may move to a diastolic model in which the prosthetic aortic heart valve will be in a closed state (such that the valve leaflets are closed). Referring to FIG. 12, diastole may start at the point indicated at line 1210 in the pressure chart. During all or a portion of the diastole phase, the valve may be in a closed state.

Referring to FIG. 13, to start the diastole phase, a corrective adjustment 1322 may be provided to a movement of the first fluid driver 106 and/or the second fluid driver 108 to move the aortic heart valve from the open state to the closed state, by rapidly varying the pressure differential such that the pressure on the downstream or outflow side of the valve is greater than the pressure on the upstream or inflow side of the valve. Such an operation may provide a period of backflow 1212 through the valve (as indicated in FIG. 12).

Under the diastole phase, the first fluid driver 106 may be configured to provide a pressure profile 1214 on the inflow side of the valve. The pressure profile 1214 may be a profile as shown in FIG. 12 or may comprise a different profile. The pressure profile 1214 may be based on one or more set pressure targets 1318 for the test fluid on the inflow side of the aortic heart valve to attain. The controller 114 may be configured to operate the first fluid driver 106 to provide a pressure profile 1214 of the test fluid on the inflow side of the aortic heart valve based on the one or more pressure targets 1318. For example, the one or more set pressure targets 1318 may be a value such as zero pressure, or other pressure value as desired. In the embodiment shown in FIGS. 12 and 13, the set pressure target is zero. The zero value may mimic the physiological state of the inflow side of the aortic heart valve during diastole, although in other embodiments other value(s) may be utilized.

The one or more set pressure targets 1318 may be input to a feedback control 1320, in addition to a measurement from the first pressure sensor 110 (the ventricular or inflow side pressure sensor). The set pressure target 1318 and the input from the first pressure sensor 110 may be provided to the first fluid driver 106 to follow. The controller 114 may be configured to operate the first fluid driver 106 to provide the pressure profile 1214 of the test fluid on the inflow side of the aortic heart valve based on feedback from the first pressure sensor 110. The feedback control 1320 may operate according to feedback parameters 1321. The feedback control 1320 may be a PID control and the feedback parameters 1321 may be PID parameters.

The feedback control 1320 may be provided to the first fluid driver 106 to assure that the first fluid driver 106 is following the prescribed one or more set pressure targets 1318.

The second fluid driver 108 during the diastole phase may continue to follow the pressure model 1308. The second fluid driver 108 during diastole may be configured to provide a pressure profile 1216 on the outflow side of the aortic heart valve. The pressure profile may be a profile as shown in FIG. 12 or may comprise a different profile as desired. Preferably, the pressure profile mimics a physiological pressure profile on the outflow or aortic side of the aortic heart valve.

During the diastole phase, the first fluid driver 106 and the second fluid driver 108 may be configured to no longer follow the displacement model, such that the first fluid driver 106 maintains a set one or more pressure targets 1318, and the second fluid driver 108 follows the pressure model 1308. The displacement model 1302 may be set to a zero or null value for the diastole phase. In one embodiment, the scaling factors 1317, 1319 may be set such that the displacement model 1302 has a zero or null value for the diastole phase. The first fluid driver 106 and second fluid driver 108, however, may follow respective feedback parameters 1327, 1329 during the diastole phase.

During the diastole phase, corrective adjustments 1322 may be provided to the first fluid driver 106 and the second fluid driver 108 to allow first fluid driver 106 and the second fluid driver 108 to adjust their respective movements to provide the desired pressure to the test fluid of the valve.

Referring to FIG. 12, a determination of coaptation of the aortic valve leaflets may occur during diastole. The determination may occur at a set point 1218, which may be based on a pressure measured by either of the pressure sensors 110, 112. The determination of coaptation may be made by operation of the camera system disclosed herein.

During the diastole phase, with the prosthetic aortic heart valve closed, the testing apparatus 100 may identify a leakage through the closed aortic heart valve. The controller 114 may be configured to identify a leakage of the aortic heart valve based on a movement of the first fluid driver 106 or the second fluid driver 108 when the aortic heart valve is in a closed state. The leakage may be identified because the first fluid driver 106 is providing a pressure profile 1214 on the inflow side of the aortic heart valve, and the second fluid driver 108 is providing a pressure profile 1216 on the outflow side of the aortic heart valve, and preferably no flow is occurring through the aortic heart valve. The first fluid driver 106 and second fluid driver 108 are not following a displacement model in the diastole phase. A leakage may thus be identified, and an amount of leakage may be determined by determining movement of the first fluid driver 106 or the second fluid driver 108. The movement of the first fluid driver 106 or the second fluid driver 108 would be caused by fluid flow through the closed valve, as the first fluid driver 106 and second fluid driver 108 are not following a displacement model and thus should not be providing a flow through the valve unless caused by leakage. The position sensors 138, 148 may be utilized to provide a signal to the controller 114 to identify movement of the fluid drivers 106, 108 and the amount and flow rate of the leakage may be determined for the aortic heart valve during the diastole phase in which the aortic heart valve is in the closed state based on the signals. A measure of the leakage may be provided, which may include an average and/or standard deviation measure of the leakage.

Referring to FIG. 13, additional feedback parameters 1323, 1325 may be provided to the feedback controls 1303, 1315. Such feedback parameters 1323, 1325 may be utilized when the first fluid driver 106 and the second fluid driver 108 are not being utilized, or are in a stationary mode. The feedback parameters 1323, 1325 may be utilized to prevent undesired movement or “humming” of the fluid drivers 106, 108 when not in use.

Figure 14:
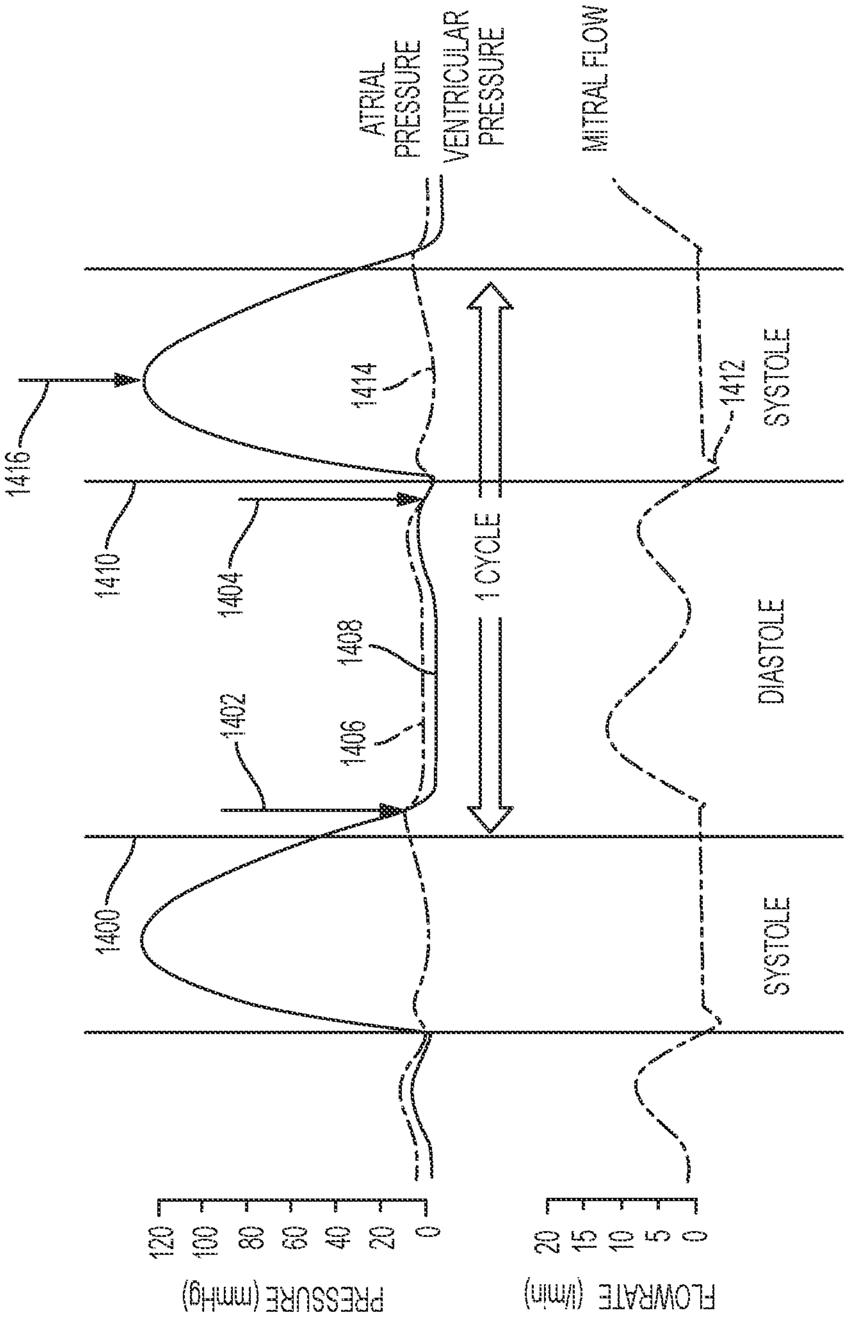
FIG. 14 illustrates a chart of an operation of a testing apparatus according to an embodiment of the present disclosure.

In addition to testing prosthetic aortic heart valves, the testing apparatus 100 may be utilized to test prosthetic mitral heart valves. The prosthetic mitral heart valves may be tested in a similar manner as discussed above regarding prosthetic aortic heart valves. FIG. 14 illustrates a pressure and flow rate chart illustrating an operation of the testing apparatus 100. The pressure and flow rate chart may be read in conjunction with the process chart shown in FIG. 15.

Figure 15:
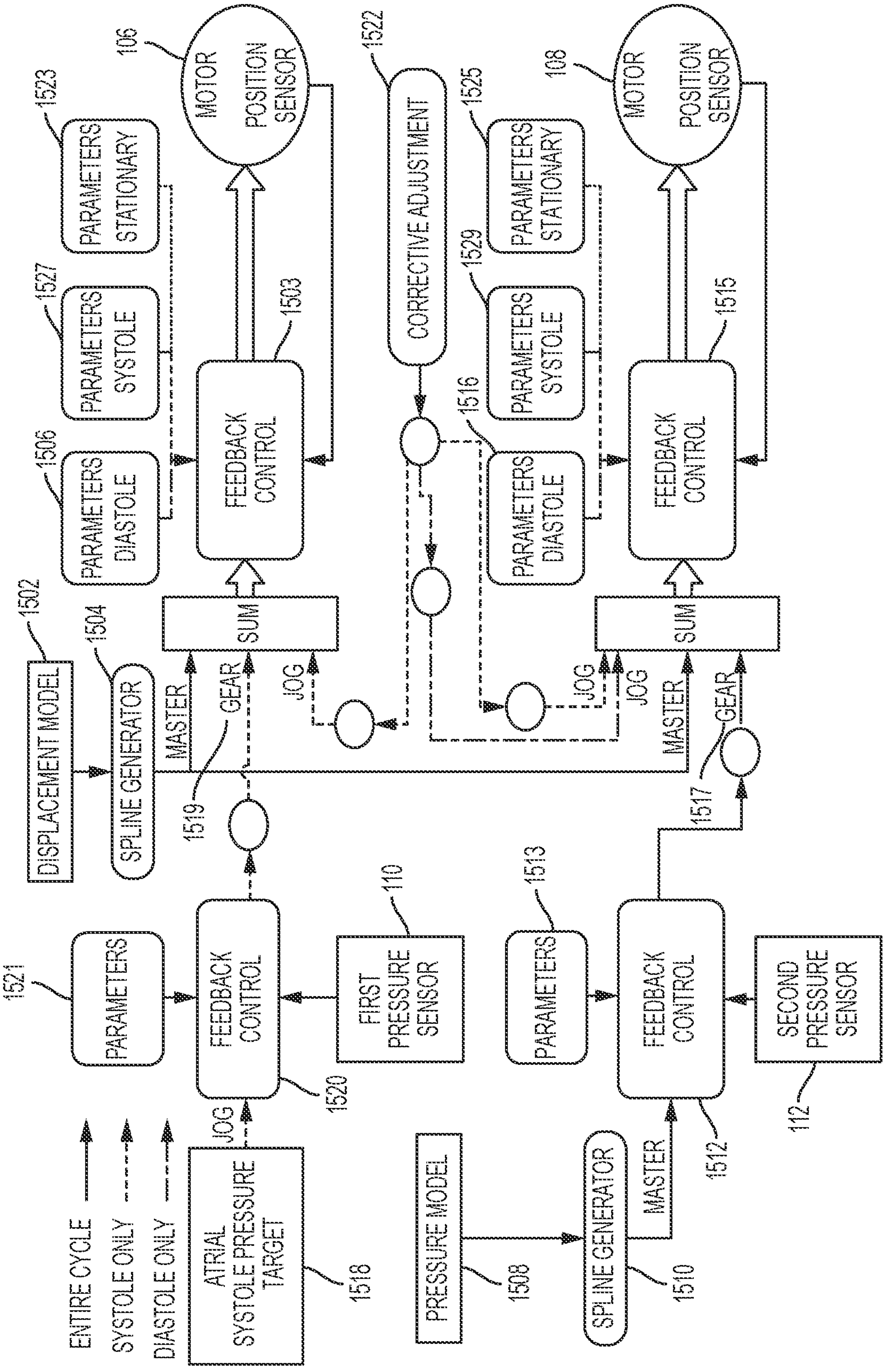
FIG. 15 illustrates a chart of an operation of a testing apparatus according to an embodiment of the present disclosure.

FIGS. 14 and 15 represent a method that may be utilized to test prosthetic mitral heart valves. Similar to the methods discussed in regard to FIGS. 12 and 13, the mitral valves may be tested under pulsatile conditions that may mimic physiological conditions applied to a mitral valve in the human heart. The testing apparatus 100 may operate the fluid drivers 106, 108 to pass fluid through the prosthetic mitral valve, which may be positioned within the testing apparatus 100 in a similar manner as the prosthetic device 124. The controller 114 marked in FIG. 1 may be utilized to operate the testing apparatus 100 and provide the processes shown in FIGS. 14 and 15 and the resulting outputs. The processor of the controller 114, or other components of the controller may be utilized to operate the testing apparatus wo and provide the process shown in FIGS. 14 and 15 and resulting outputs, and may utilize a software method or other method to operate the testing apparatus 100 and provide the process shown in FIGS. 14 and 15 and resulting outputs.

The prosthetic mitral heart valve may be configured to pass fluid from the upstream position (or inflow side) discussed in regard to FIG. 1 to the downstream position (or outflow side).

Under testing of the mitral heart valve, the first fluid driver 106 may be considered an atrial fluid driver, and the second fluid driver 108 may be considered a ventricular fluid driver. The first pressure sensor 110 may be configured to determine the atrial pressure (or pressure on the inflow side), and the second pressure sensor 112 may be configured to determine the ventricular pressure (or pressure on the outflow side).

The testing apparatus 100 may operate as follows. Referring to FIG. 14, a start (indicated by line 1400) of a diastole phase may initiate a pressure gradient between the atrium and ventricle (the pressure gradient is marked between lines 1402 and 1404). During all or a portion of diastole, the valve may be in an opened state, with the valve opened to pass test fluid therethrough in the outflow direction.

Referring to FIG. 15, the operation under the diastole phase may start in a similar manner as aortic valve testing, with a displacement model 1502 being provided to the first fluid driver 106 (the atrial fluid driver) and to the second fluid driver 108 (the ventricular fluid driver). The displacement model 1502 may be smoothed by a spline generator 1504 prior to being received by the first fluid driver 106 and the second fluid driver 108. The displacement model 1502 may indicate a prescribed movement for the first fluid driver 106 and for the second fluid driver 108.

The first fluid driver 106 (the atrial fluid driver) may operate based on the displacement model 1502. As such, the first fluid driver 106 follows a prescribed movement of position and speed based on the displacement model 1502, similar to the operation of the first fluid driver 106 described above regarding aortic valve testing. The displacement model 1502 may indicate the amount of displacement of the first fluid driver 106 (for example, the displacement of the piston 134 of the first fluid driver) as well as the timing of the displacement (for example, the speed at which the piston 134 moves). A feedback control 1503 may be provided to the first fluid driver 106 based on feedback from the position sensor 138 of the first fluid driver 106. The position sensor 138 may be configured to provide the position and movement (e.g., speed of movement) of the first fluid driver 106 (including the piston 134 of the first fluid driver).

During the diastole phase, the feedback control 1503 may utilize feedback parameters 1506 that are configured for use by the feedback control 1503 during the diastole phase. The feedback parameters 1506 may be utilized by the feedback control 1503 to indicate whether the first fluid driver 106 is following the prescribed displacement model 1502 and to provide feedback to allow the first fluid driver 106 to follow the displacement model 1502. The feedback control 1503 may comprise a PID control and the feedback parameters 1506 may comprise PID parameters.

During the diastole phase, the pressure on the upstream or inflow side of the valve may be determined via the first pressure sensor 110 during this operation. However, similar to the systole phase of the aortic valve testing, the feedback from the first pressure sensor 110 is not provided to the first fluid driver 106. The pressure profile 1406 shown in FIG. 14 may remain an artifact of the prescribed movement of the first fluid driver 106.

Referring to FIG. 15, the second fluid driver 108 (the ventricular fluid driver) under the diastole phase may receive the input from the displacement model 1502. The second fluid driver 108 may be configured to follow the displacement model 1502 to allow for a desired flow through the mitral heart valve.

The second fluid driver 108, however, may also receive input from a pressure model 1508. The controller 114 accordingly is configured to move the second fluid driver 108 based on a pressure model 1508 when the mitral heart valve is in an open state, similar to the operation of the second fluid driver 108 for aortic valve testing. The input from the pressure model 1508 may be smoothed by a spline generator 1510. The pressure model 1508 may comprise one or more pressures to be provided by the second fluid driver 108. The pressure may be provided by the second fluid driver 108 moving out of sync (asynchronously) with the first fluid driver 106 to cause the second fluid driver 108 to apply a pressure to the test fluid. Referring to FIG. 14, the pressure model 1508 may define a pressure profile 1408 (shown in solid line) for the second fluid driver 108 to provide on the ventricular side (or outflow side) of the mitral heart valve during the diastole phase. The pressure profile 1408 may comprise a back pressure to be provided by the second fluid driver 108 during the diastole phase, and may mimic a physiological back pressure profile provided by the human heart during the diastole phase. The controller 114 may be configured to operate the second fluid driver 108 to provide a back pressure profile of the test fluid on the outflow side of the mitral heart valve when the mitral heart valve is in the open state.

The input from the smoothed pressure model 1508 may be provided to a feedback control 1512. The feedback control 1512 may receive input from the second pressure sensor 112. The input from the second pressure sensor 112 may be provided to the feedback control 1512 to allow for feedback regarding the pressure on the ventricular side of the mitral valve. The feedback control 1512 may utilize feedback parameters 1513 that are configured for use by the feedback control 1512. The feedback control 1512 may comprise a PID control and the feedback parameters 1513 may comprise PID parameters.

The feedback from the second pressure sensor 112 may be utilized to allow the second fluid driver 108 to provide the desired pressure profile 1408 on the ventricular side (or outflow side) of the mitral heart valve, and control the movement of the second fluid driver 108 to provide the desired pressure profile 1408.

The output of the feedback control 1512 may be combined with the prescribed movement of the displacement model 1502 and input to a feedback control 1515 of the second fluid driver 108. A scaling factor 1517 may be utilized to set the proportionate value of the feedback control 1512 compared to the value provided by the displacement model 1502. These combined parameters may be provided to the feedback control 1515 of the second fluid driver 108.

The second fluid driver 108 may operate based on the displacement model 1502. The displacement model 1502 may indicate the displacement of the second fluid driver 108 (for example, the displacement of the piston 144 of the second fluid driver). The position sensor 148 may be configured to provide the position and movement (e.g., speed of movement) of the second fluid driver 108 (including the piston 144 of the second fluid driver). The second fluid driver 108 may be configured to provide an opposite and equal displacement of the test fluid to allow the test fluid to flow through the mitral valve in a prescribed manner (although in an asynchronous manner to allow for the back pressure of the second fluid driver 108 based on the input from the feedback control 1512). The opposite and equal displacement results because the flow channel 105 is entirely filled with test fluid, and to allow for a flow of fluid, an equal and opposite amount of displacement by the second fluid driver 108 must be provided.

The feedback control 1515 may be provided to the second fluid driver 108 based on feedback from the position sensor 148 of the second fluid driver 108. During the diastole phase, the feedback control 1515 may utilize feedback parameters 1516 that are configured for use by the feedback control 1515 during the diastole phase. The feedback control 1515 may comprise a PID control and the feedback parameters 1516 may comprise PID parameters. The second fluid driver 108 accordingly may move based on the displacement model 1502 to provide a desired flow through the valve and may move based on a pressure model 1508 to provide a desired back pressure to the test fluid of the valve, with feedback provided by the pressure sensor 112. The pressure on the downstream or outflow side of the valve may be determined via the second pressure sensor 112 during this operation.

A corrective adjustment 1522 may be provided to the second fluid driver 108 during the diastole phase to allow the second fluid driver 108 to adjust its movement to provide a desired back pressure to the test fluid of the valve. The corrective adjustment 1522 may comprise an additional control that is provided to the second fluid driver 108 to account for a non-linear response of the pressure on the downstream or outflow side of the mitral heart valve to the movement of the second fluid driver 108. As such, the feedback controls 1515, 1512 may be unable to account for the non-linear response of the pressure on the downstream or outflow side of the valve to the movement of the second fluid driver 108 and the corrective adjustment 1522 may be utilized to provide the desired back pressure.

Upon operation of the first fluid driver 106 and the second fluid driver 108 during the diastole phase, the first pressure sensor 110 may be configured to measure the pressure of the test fluid on the atrial side (inflow side) of the mitral heart valve, and the second pressure sensor 112 may be configured to measure the pressure of the test fluid on ventricular side (outflow side) of the mitral heart valve. A pressure gradient may be determined between the measured atrial pressure on the inflow side (measured by the first pressure sensor no) and the measured ventricular pressure on the outflow side (measured by the second pressure sensor 112) during the entire positive differential pressure period of the measured atrial pressure and the measured ventricular pressure, as marked between arrows 1402 and 1404. The controller 114 may be configured to determine, based on measurements of the first pressure sensor 110 and the second pressure sensor 112, a pressure differential between the test fluid on the inflow side and the test fluid on the outflow side of the mitral valve when the mitral valve is in an open state.

The pressure gradient may be determined for the entire positive differential pressure period of the measured atrial pressure and the measured ventricular pressure. The controller 114 may be configured to determine, based on the measurements of the first pressure sensor 110 and the second pressure sensor 112, the period in which the pressure of the test fluid on the inflow side is greater than the pressure of the test fluid on the outflow side.

The pressure gradient may be utilized in the equation listed below, and discussed above, to determine effective orifice area (EOA) of the aortic valve:

$$EOA = \frac{q_{v_{RMS}}}{51.6\sqrt{\frac{\Delta p}{\rho}}}$$

The controller 114 may be configured to determine the effective orifice area of the mitral valve based on the flow and based on the pressure differential between the test fluid on the inflow side and the test fluid on the outflow side of the mitral valve during the positive pressure period.

The flow through the mitral valve may be known based on the movement of the first fluid driver 106 and the second fluid driver 108. For example, the geometry of the pistons 134, 144 may be known such that the displacement of the pistons 134, 144 provided by the position sensors 138, 148 is used to determine the flow through the mitral valve. Similar to aortic valve testing, no flow meters or other flow sensors are utilized under this method.

The measurement of effective orifice area (EOA) may be provided as an output upon the first instance of the diastole phase occurring for the mitral heart valve, or upon multiple instances of the diastole phase occurring or being measured for the mitral heart valve. For example, multiple cycles of the diastole phase and systole phase may occur before the measure of effective orifice area is provided. The measurement of effective orifice area (EOA) may be provided as a quantitative value, and may include an average and/or standard deviation value for the mitral heart valve.

At the conclusion of the diastole phase, the testing apparatus 100 may move to a systolic model in which the mitral valve will be in a closed state (such that the valve leaflets are closed) during all or a portion of systole. Referring to FIG. 14, systole may start at the point indicated at line 1410 in the pressure chart.

Referring to FIG. 15, to start the systole phase, a corrective adjustment 1522 may be provided to a movement of the first fluid driver 106 and/or the second fluid driver 108 to move the mitral heart valve from the open state to the closed state, by rapidly varying the pressure differential such that the pressure on the downstream or outflow side of the valve is greater than the pressure on the upstream or inflow side of the valve. Such an operation may provide a period of backflow 1412 through the valve (as indicated in FIG. 14).

Under the systole phase, the first fluid driver 106 may be configured to provide a pressure profile 1414 on the inflow side of the valve. The pressure profile 1414 may be a profile as shown in FIG. 14 or may comprise a different profile. The pressure profile 1414 may be based on one or more set pressure targets 1518 for the test fluid on the inflow side of the mitral valve to attain. The controller 114 may be configured to operate the first fluid driver 106 to provide a pressure profile 1414 of the test fluid on the inflow side of the mitral heart valve based on one or more pressure targets. For example, the one or more set pressure targets 1518 may have a pressure value as desired. In the embodiment shown in FIG. 14, multiple set pressure targets are provided. The multiple set pressure targets may mimic the physiological state of the inflow side of the mitral heart valve during systole, although in other embodiments other value(s) may be utilized.

The one or more set pressure targets 1518 may be input to a feedback control 1520, in addition to a measurement from the first pressure sensor 110 (the atrial or inflow pressure sensor). The set pressure target 1518 and the input from the first pressure sensor no may be provided to the first fluid driver 106 to follow. The controller 114 may be configured to operate the first fluid driver 106 to provide the pressure profile 1414 of the test fluid on the inflow side of the mitral heart valve based on feedback from the first pressure sensor 110. The feedback control 1520 may operate according to feedback parameters 1521. The feedback control 1520 may be a PID control and the feedback parameters 1521 may be PID parameters.

The feedback control 1520 may be provided to the first fluid driver 106 to assure that the first fluid driver 106 is following the prescribed set one or more pressure targets 1518.

The second fluid driver 108 during the systole phase may continue to follow the pressure model 1508. The second fluid driver 108 may be configured to provide a pressure profile on the outflow side of the valve. The pressure profile may be a profile as shown in FIG. 14, or may comprise a different profile as desired. Preferably, the pressure profile mimics a physiological profile on the outflow or ventricular side of the mitral valve.

During the systole phase, the first fluid driver 106 and the second fluid driver 108 may be configured to no longer follow the displacement model, such that the first fluid driver 106 maintains a set one or more pressure targets 1518, and the second fluid driver 108 follows the pressure model 1508. The displacement model 1502 may be set to a zero or null value for the systole phase. In one embodiment, the scaling factors 1517, 1519 may be set such that the displacement model 1502 has a zero or null value for the systole phase. The first fluid driver 106 and second fluid driver 108, however, may follow respective feedback parameters 1527, 1529 during the systole phase.

During the systole phase, corrective adjustments 1522 may be provided to the first fluid driver 106 and the second fluid driver 108 to allow first fluid driver 106 and the second fluid driver 108 to adjust their respective movements to provide the desired pressure to the test fluid of the valve.

Referring to FIG. 14, a determination of coaptation of the mitral valve leaflets may occur during the systole phase. The determination may occur at a set point 1416, which may be based on a pressure measured by either of the pressure sensors 110, 112. The determination of coaptation may be made by operation of the camera system disclosed herein.

During the systole phase, with the mitral heart valve closed, the testing apparatus 100 may identify a leakage through the closed mitral heart valve in the same manner as disclosed above regarding aortic valve testing. For example, the leakage may be identified based on movement of the first fluid driver 106 or the second fluid driver 108 because the first fluid driver 106 and second fluid driver 108 are not following a displacement model during the systole phase. The controller 114 may be configured to identify a leakage of the mitral heart valve based on a movement of the first fluid driver 106 or the second fluid driver 108 when the mitral heart valve is in a closed state.

Referring to FIG. 15, additional feedback parameters 1523, 1525 may be provided to the feedback controls 1503, 1515. Such feedback parameters 1523, 1525 may be utilized when the first fluid driver 106 and the second fluid driver 108 are not being utilized, or are in a stationary mode. The feedback parameters 1523, 1525 may be utilized to prevent undesired movement or "humming" of the fluid drivers 106, 108 when not in use.

The operations discussed herein may be modified as desired with desired pressure models, pressure profiles, and displacement models, or other parameters of the system as desired. For example, any of the models, profiles, or parameters may be based on the type of valve being tested in the testing apparatus 100. If a user were to input the type of prosthetic device to be tested into the controller 114, the controller 114 may be configured to automatically load and apply the models, profiles, or parameters or other features of the testing, and execute the testing as desired.

The displacement models 1302, 1502, pressure models 1308, 1508, pressure profiles, one or more pressure targets 1318, 1518, and parameters 1321, 1521, 1306, 1506, 1327, 1527, 1323, 1523, 1316, 1516, 1329, 1529, 1325, 1525, 1313, 1513, as well as the corrective adjustments 1322, 1522 may be configured for the type of prosthetic device being tested, and may be stored in the memory of the controller 114 and retrieved by the controller 114 for use for that particular type of prosthetic device. The parameters 1321, 1521, 1306, 1506, 1327, 1527, 1323, 1523, 1316, 1516, 1329, 1529, 1325, 1525, 1313, 1513 may be configured to be automatically retrieved based on the systole or diastole phase of operation, for example the feedback controls 1303, 1315, 1503, 1515 may be configured to automatically switch between systole parameters 1306, 1527, 1316, 1529, and diastole parameters 1327, 1506, 1329, 1516 during operation.

In embodiments, other forms of feedback control other than PID controls may be utilized. In other embodiments, other forms of feedback parameters than PID parameters may be utilized.

The pressure models, pressure profiles, and displacement models, or other parameters of the system may be varied as desired. For example, a custom or modified version of the testing operations may be provided as desired. Custom flow or pressure curves may be provided, among other parameters (e.g., length or number of testing cycles).

The pressure and flow profiles shown in FIGS. 12 and 14 and methods of operation shown in FIGS. 13 and 15 are intended to be exemplary, and may be modified as desired.

In embodiments, prosthetic valves other than aortic valves and mitral valves may be tested under similar methods as disclosed herein regarding aortic and mitral valves. The methods disclosed herein are not limited to aortic valves or mitral valves.

The controller 114 may be configured to automatically provide the testing operations disclosed herein. For example, the controller 114 may be configured to automatically move the testing apparatus 100 to the closed configuration, to fill the flow chamber 105, and provide a testing operation of the prosthetic device as desired.

The testing cycles disclosed in regard to FIGS. 12-15 may occur for one cycle (one systole and diastole phase) or multiple cycles as desired. The timing of each cycle may occur according to the timing of an actual human heartbeat, and one cycle may occur in less than one second, or other time as desired.

The output of the testing operations is not limited to effective orifice area (EOA) or leakage, but may also include other flow properties of the tested prosthetic valves such as pressure gradient across the valve or other hydrodynamic measurements. The output may be provided to the display screen 208 of the control terminal 202, or other display screen as desired. The output may be provided as a quantitative amount, or in certain embodiments an indicator such as indicator 1110 shown in FIG. 11 may be utilized to provide a visual pass/fail output or the like. As discussed, the processor 1100 may utilize one or more thresholds to automatically determine and indicate whether the tested prosthetic valve is acceptable. The processor 1100 may provide an output based on any of the measured properties of the prosthetic valve (for example, pressure gradient, EOA, or leakage, among others).

The methods of operation of the testing apparatus 100 may be varied, excluded, or modified in other embodiments as desired.

Beneficially, the methods of the testing apparatus 100 may provide for pulsatile physiological conditions for the tested valve. The dual drive arrangement may reduce complexity of the apparatus, and may provide for ease of use. The use of flow meters or other flow sensors may be excluded, which simplifies the operation of the apparatus.

The coaptation determination for the prosthetic valves may occur through use of the cameras 132, 184, 414, 416 marked in FIG. 4. The coaptation determination may occur during the testing cycle during the closed states of the prosthetic valves. Such determinations may be made, for example, at points 1218 and 1416 as shown in FIGS. 12 and 14, or at another point as desired. The controller 114, or the processor 1100 of the controller, may be configured to automatically perform the coaptation determination at the desired point(s).

The cameras 132, 184, 414, 416 may be configured to view the prosthetic valve leaflets when the prosthetic valve is closed to determine the coaptation of the valve leaflets. The cameras 184, 414, 416 may be configured to view the prosthetic valve positioned in the flow channel 105, through the wall 118. The cameras 132, 184, 414, 416 may be configured to provide one or more images of the prosthetic valve leaflets that are used by the controller 114, or the processor 1100 of the controller, to determine a property of coaptation of the leaflets of the prosthetic valve when the valve leaflets are in the closed state.

Figure 16:
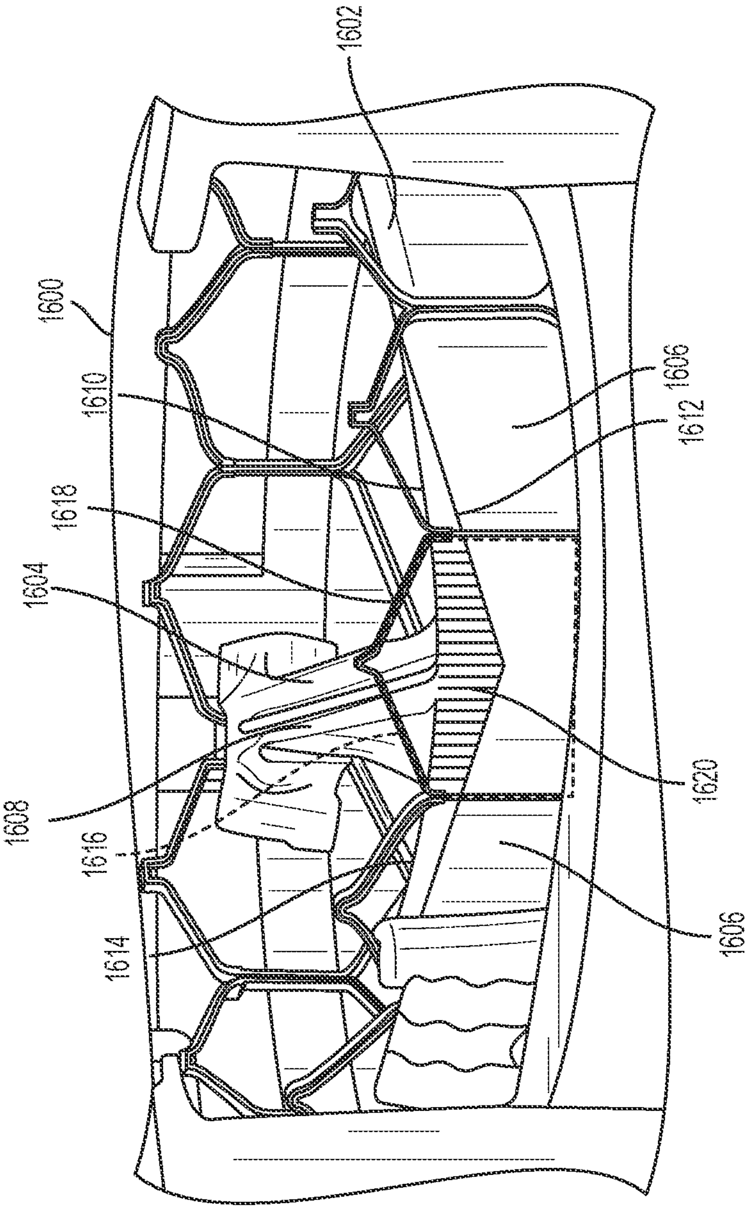
FIG. 16 illustrates a side view of a prosthetic heart valve according to an embodiment of the present disclosure.

FIG. 16, for example, illustrates an image 1600 comprising a side view of a prosthetic heart valve 1602 that may be produced by one of the side view cameras 184, 414, 416. The prosthetic heart valve 1602 may include three leaflets 1604, 1606, 1608 that are in a closed state. An edge 1610, 1612, 1614 of the respective leaflets 1604, 1606, 1608 is shown to have a coaptation property comprising a mismatch. A mismatch of the leaflets 1604, 1606, 1608 may comprise an undesired coaptation of the heart valve 1602.

Upon one or more of the side view cameras 184, 414, 416 providing one or more images of the prosthetic heart valve 1602, the testing apparatus 100 may be configured to automatically identify and define a region of interest 1616 for the viewed image. The processor 1100 (which may comprise an image processor) of the controller 114 may be configured to receive an input of the image from one of the side view cameras 184, 414, 416, and may be configured to process the image to automatically identify and define the region of interest 1616. In other embodiments, other processors may be utilized for the image processing methods.

The region of interest 1616 may be automatically defined based on an indicator 1618 present in the image. For example, as shown in FIG. 16, the indicator 1618 may comprise an appearance of a portion of the prosthetic valve 1602, such as an appearance of the frame for a catheter-implanted valve. The processor 1100 may be configured to identify the indicator 1618 and define the region of interest 1616 based on the location and presence of this indicator 1618. The processor 1100 may be configured to automatically adjust image properties, such as brightness or contrast to optimize a view of the edges of the leaflets in certain embodiments.

Upon identification and definition of the region of interest 1616, the processor 1100 may be configured to automatically measure a property of the coaptation of the valve in the region of interest 1616. The property may be a measure of mismatch of the leaflets. The property may be an image distance (for example a pixel distance), that may be converted to a real distance based on a scaling. The scaling may be provided by use of a calibration device, as discussed herein. The processor 1100 may be configured to measure the image distance on a pixel by pixel basis. The coaptation may be determined by measuring the distance between the edges 1610, 1614 of the leaflets 1604, 1608, with the edge 1612 of the leaflet 1606. The coaptation may be determined as a distance between edges 1610, 1614 of the leaflets 1604, 1608, with the edge 1612 of the leaflet 1606, as indicated by the hashed lines 1620 shown in FIG. 16. In one embodiment, the coaptation may be determined as the longest length (in pixel) measured, for example, the longest hashed line 1620 shown in FIG. 16.

The processor 1100 may be configured to compare the measurement of the coaptation with a standard for acceptable coaptation, and provide an indication of whether the prosthetic valve 1602 is acceptable or not (for example, through the indicator 1110 discussed in regard to FIG. 11). The user, accordingly, may not make a determination of suitable coaptation in certain embodiments. In one embodiment, however, the user may confirm or make a separate determination of suitable coaptation based on viewing the images on the display screen 208 or the like. In one embodiment, the processor 1100 may output a property of the coaptation, for example, a quantitative measure of the coaptation may be provided (e.g., the real distance between the edges 1610, 1614 of the leaflets 1604, 1608, with the edge 1612 of the leaflet 1606). Other statistical measures may be provided, such as an average and/or standard deviation of any of the coaptation properties of the valve. The measure of coaptation may be provided for each side image provided of the prosthetic valve 1602 by each side camera (184, 414, 416) and for each leaflet 1604, 1606, 1608 of the prosthetic valve 1602. The measure of coaptation may be provided upon a single cycle being provided of the valve in a closed state, or multiple cycles, with statistical measures such as an average and/or standard deviation being provided for the coaptation measures of the valve.

The processor 1100 may be configured to automatically provide the measurement of the coaptation based on automatic production of the one or more images of the prosthetic valve 1602 taken by the camera system. The processor 1100 may be configured to automatically process the images and determine the property of coaptation of the valve 1602.

Figure 18:
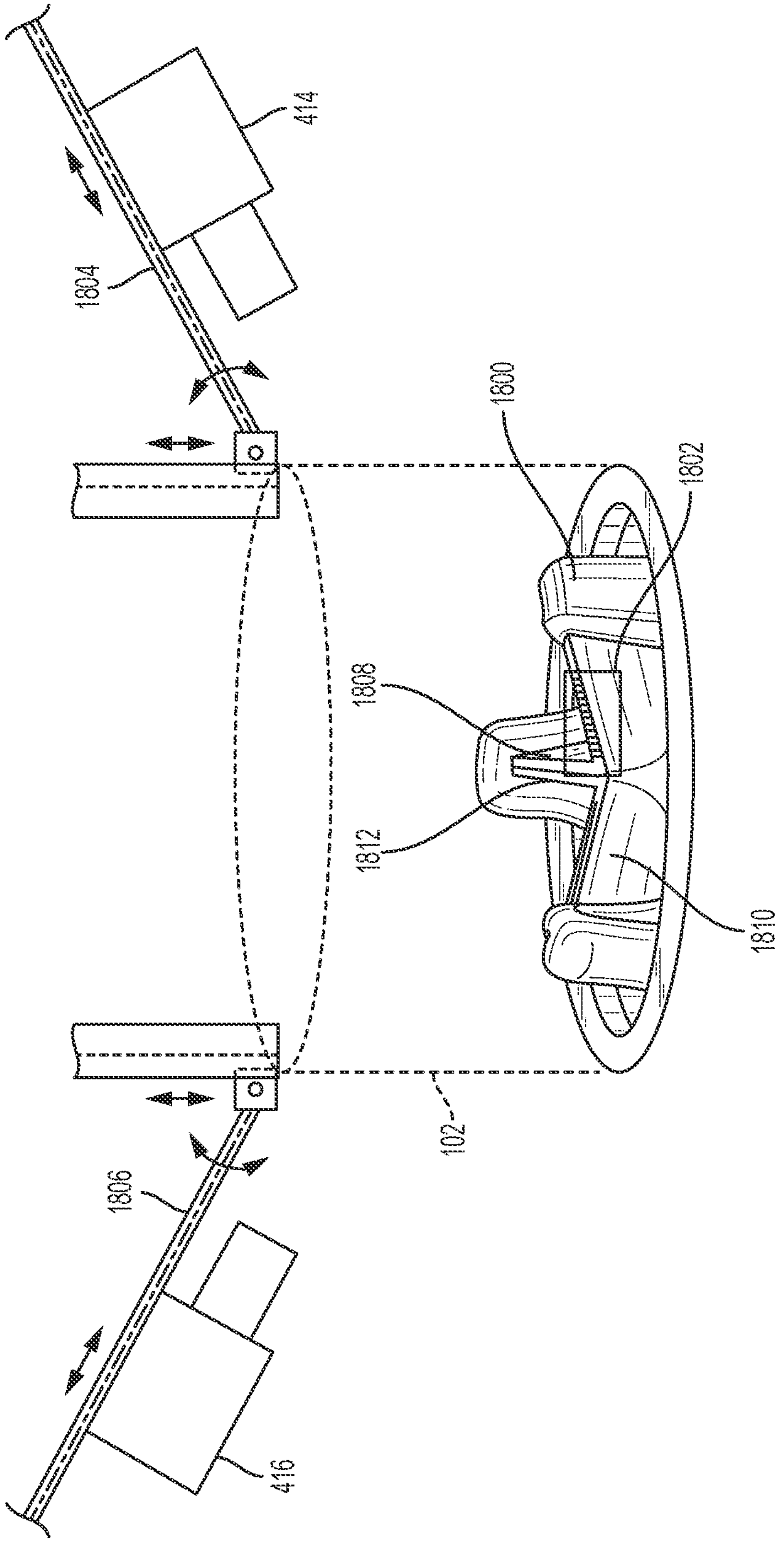
FIG. 18 illustrates a schematic of camera mountings and a side view of a prosthetic heart valve according to an embodiment of the present disclosure.

In one embodiment, the identification and definition of the region of interest may occur manually by a user. For example, in a surgically implanted valve 1800, as shown in FIG. 18, the user may manually define the region of interest 1802 if no clear indicator of the valve 1800 is present. In one embodiment, the user may be able to manually select the region of interest as desired, or may override the automatic detection of the region of interest by the processor 1100. The automatic determination of the property of coaptation may occur following the identification of the region of interest.

Figure 17:
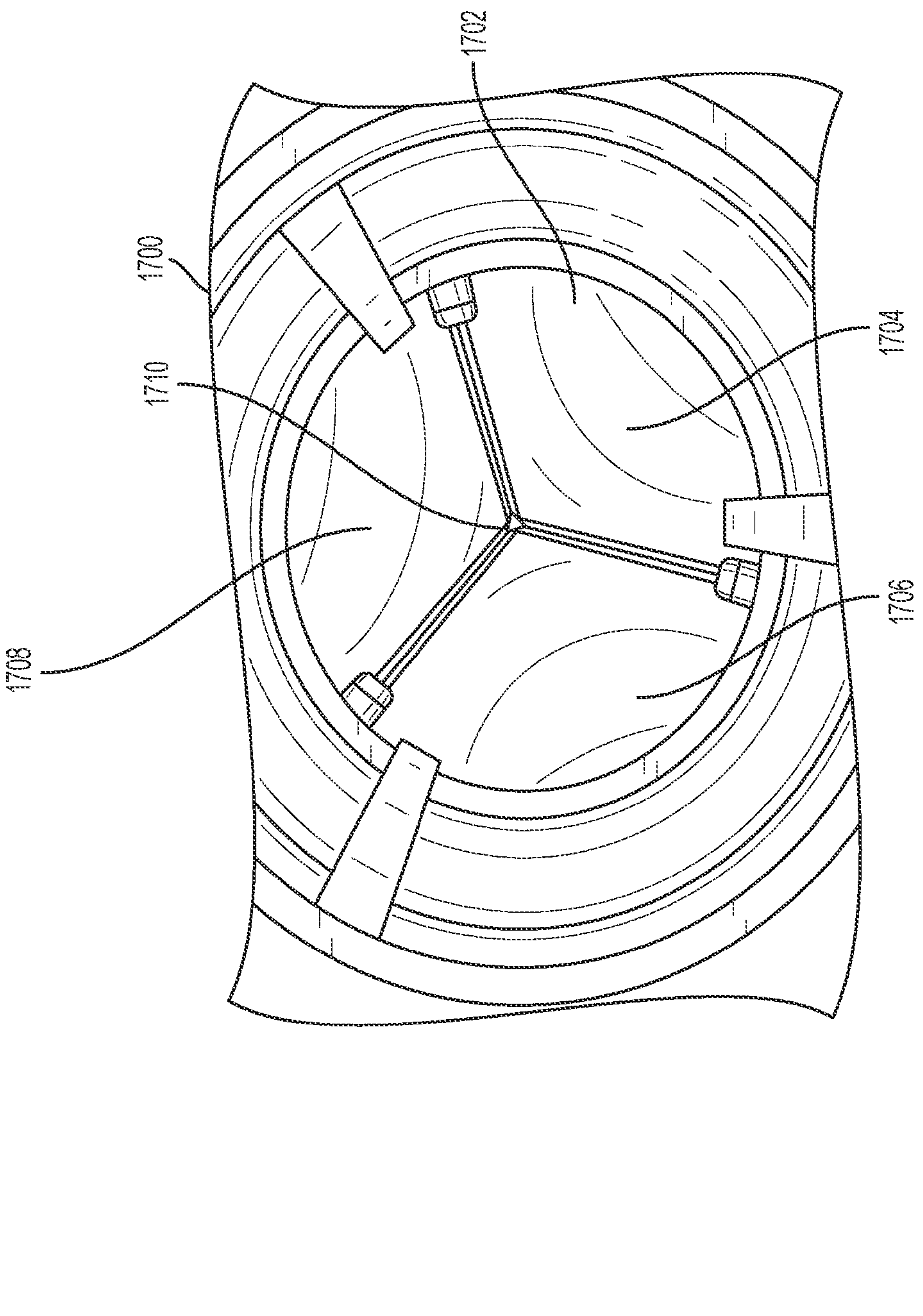
FIG. 17 illustrates an axial view of a prosthetic heart valve according to an embodiment of the present disclosure.

Referring to FIG. 17, the axial camera 132 may provide an axial view and axial image 1700 of a prosthetic valve 1702. FIG. 17 illustrates an axial view of the prosthetic valve 1702 in a closed state. The prosthetic valve 1702 may include three leaflets 1704, 1706, 1708 that are in the closed state. A central opening 1710, however, is provided of the leaflets 1704, 1706, 1708. The axial view may allow for measurement of the size of the central opening 1710 of the valve 1702 when the valve 1702 is in the closed state. The processor 1100 may be configured to automatically provide a measurement of the size of the central opening 1710 of the valve 1702, and thus provide a property of coaptation of the prosthetic valve 1702. Similar to the processes discussed in regard to FIGS. 16 and 18, the processor 1100 may be configured to automatically determine a region of interest and automatically measure the size of the central opening 1710 on a pixel by pixel basis. The image distance may be converted to a real distance utilizing methods disclosed herein. The measurement of the size of the central opening 1710 may occur during the coaptation measurement of the prosthetic valve 1702, and may occur at the same time the side images of the valve 1702 are taken.

Referring to FIG. 18, the side cameras 414, 416 (and 184 not pictured) may be coupled to the testing apparatus 100 with a fixed mount, or may be coupled to the testing apparatus 100 with a movable mount. FIG. 18 illustrates an embodiment in which one or more of the side cameras 414, 416, 184 may be coupled to the testing apparatus 100 with a movable mount 1804, 1806 such that movement axially, as well as radially, or a combination thereof (as indicated by the movement lines in FIG. 18) may be provided by the side cameras 414, 416, 184 to vary the side view of the prosthetic valve 1800. In one embodiment, the side cameras 414, 416, 184 may be configured to be moved automatically by the controller 114 to provide a desired view of the valve leaflets 1808, 1810, 1812. Servos or the like may move the side cameras 414, 416, 184 and the mounts 1804, 1806 may include rails or pivots for the side cameras 414, 416, 184 to move with. In one embodiment, mirrors that are used by the side cameras 414, 416, 184 to view the valve 1800 may be moveable, and moved automatically by the controller 114 to provide a desired view of the valve leaflets 1808, 1810, 1812. In one embodiment, the user may be able to manually provide an input to the controller 114 to move the side cameras 414, 416, 184 or the view of the side cameras 414, 416, 184 to the desired position. In one embodiment, the entire test chamber 102 may be configured to rotate, either manually or via servo control (controlled by the controller 114), such that the view of the valve leaflets are not blocked by any air bubbles.

The images of the valves 1602, 1702, 1800 discussed herein are taken by the camera system of the testing apparatus 100 and may be affected by optical distortion caused by the presence of the test fluid within the flow chamber 105. The processor 1100 may be configured to determine a pixel by pixel distance between portions of an image to determine coaptation, however, such image distances may not accurately correspond to a real distance for all portions of the image due to the possible optical distortion, as well as due to the cylindrical geometry of the prosthetic valves. Due to the cylindrical geometry, the scaling of the image distance to the real distance may be different for different radial distances of the portions of the prosthetic valve. As such, the measurements of the coaptation properties provided by the camera system may need to be calibrated to produce a quantitative measure of real distance between portions of the image and portions of the prosthetic valves, particularly the valve leaflets.

Figure 19:
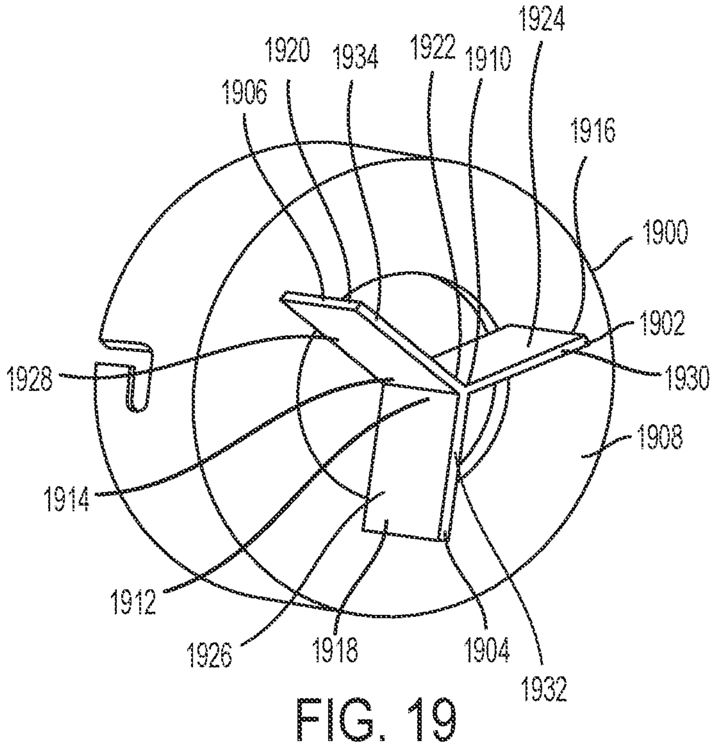
FIG. 19 illustrates a perspective view of a calibration device according to an embodiment of the present disclosure.

FIG. 19 illustrates a side perspective view of an embodiment of a calibration device 1900 that may be utilized with the testing apparatus 100. The calibration device 1900 may be utilized in a method of determining a scaling between an image distance and a real distance based on one or more images of the calibration device 1900. The method may include determining a property, based on the scaling, of one or more leaflets of a prosthetic valve shown in one or more images.

The calibration device 1900 may include a plurality of walls 1902, 1904, 1906 spaced from each other. The plurality of walls 1902, 1904, 1906 may be coupled to a base 1908 and may extend axially from the base 1908. The plurality of walls 1902, 1904, 1906 may extend radially outward from each other.

The plurality of walls 1902, 1904, 1906 may each include a respective coupling portion 1910, 1912, 1914, and a respective end portion 1916, 1918, 1920. The plurality of walls 1902, 1904, 1906 may be coupled to each other at the coupling portion 1910, 1912, 1914 and may extend radially outward from the coupling portion 1910, 1912, 1914 to the respective end portion 1916, 1918, 1920. The plurality of walls 1902, 1904, 1906 may couple to each other at a central portion 1922 of the calibration device 1900.

Figure 20:
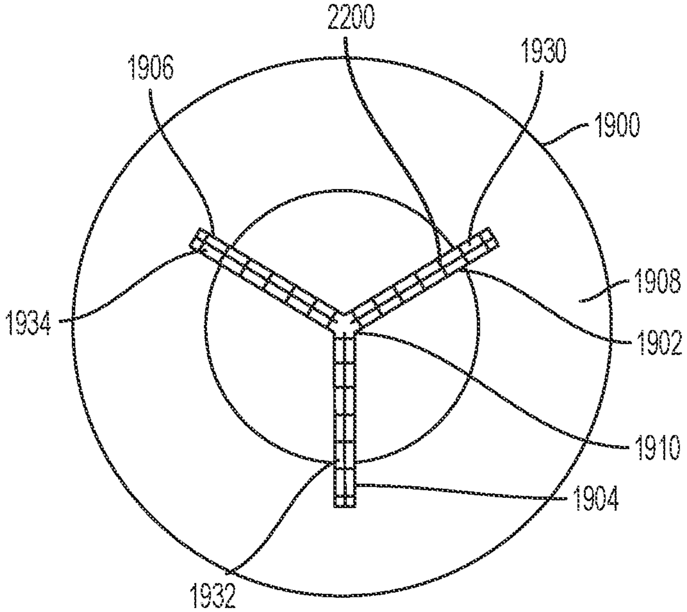
FIG. 20 illustrates a top view of a calibration device according to an embodiment of the present disclosure.

The walls 1902, 1904, 1906 may include three walls, and may be spaced substantially equidistant from each other. The walls 1902, 1904, 1906 may extend radially outward from the central portion 1922 at a substantially equal angle such that the end portions 1916, 1918, 1920 of the walls 1902, 1904, 1906 are positioned equidistant from each other. The walls 1902, 1904, 1906 may extend at a substantially equal angle of about 120 degrees from each other. The walls 1902, 1904, 1906 may form a Y-shape, as shown in FIGS. 19 and 20.

Each wall 1902, 1904, 1906 may be configured to extend in the same plane as a contact plane of a leaflets of a prosthetic valve. For example, the contact planes of the valve 1702 shown in FIG. 17 constitute the planes extending out of the page at which the leaflets 1704, 1706, 1708 contact each other. The walls 1902, 1904, 1906 are configured to extend in the same plane as a contact plane so that calibration of the view of the prosthetic valve along the contact planes may be provided.

In other embodiments, other configurations of the walls of the calibration device may be provided. For example, if the calibration device is configured to calibrate an image for a four leaflet valve or a five leaflet valve, the number and orientation of the walls of the calibration device may be modified accordingly. Preferably, the walls each extend in the same plane as a contact plane of a leaflets of a prosthetic valve.

Each wall 1902, 1904, 1906 may include side surfaces 1924, 1926, 1928 (the opposite side surfaces are not shown in FIG. 19) and top surfaces 1930, 1932, 1934.

Figure 21:
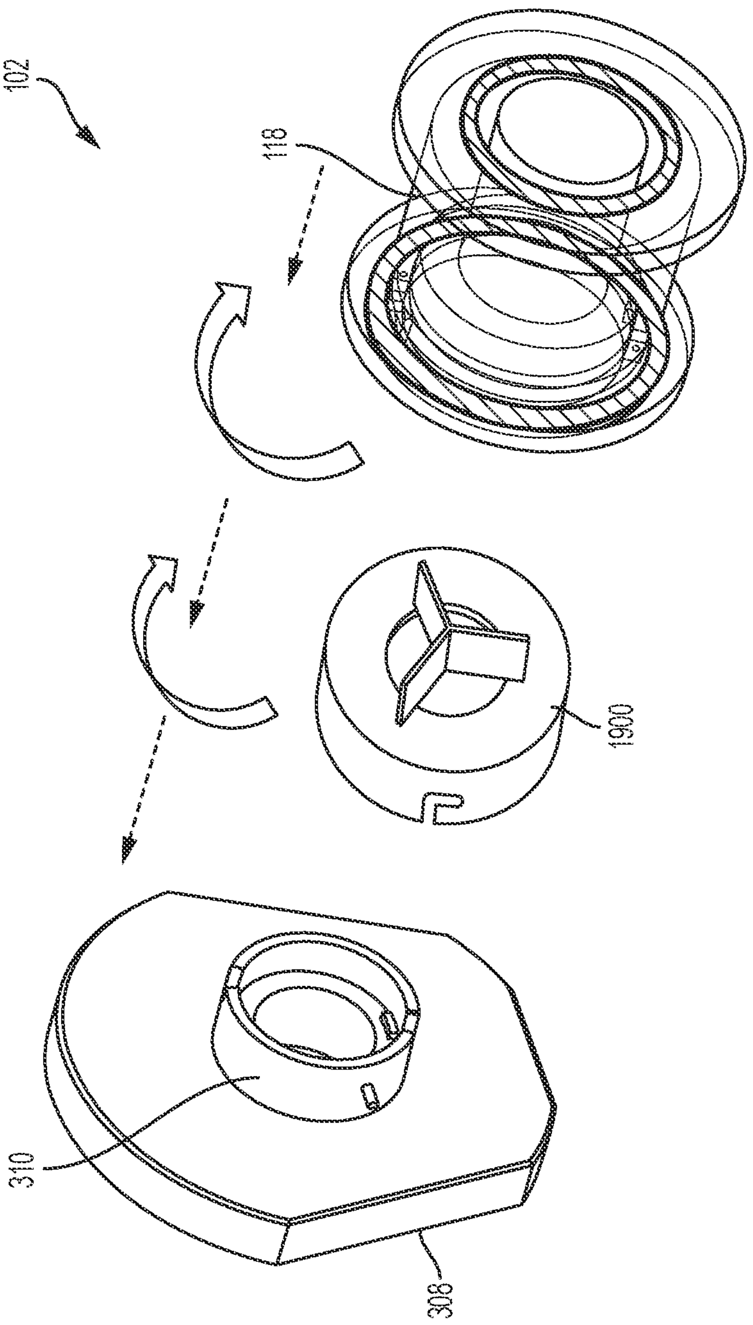
FIG. 21 illustrates a perspective expanded view of a test chamber according to an embodiment of the present disclosure.
Figure 22B:
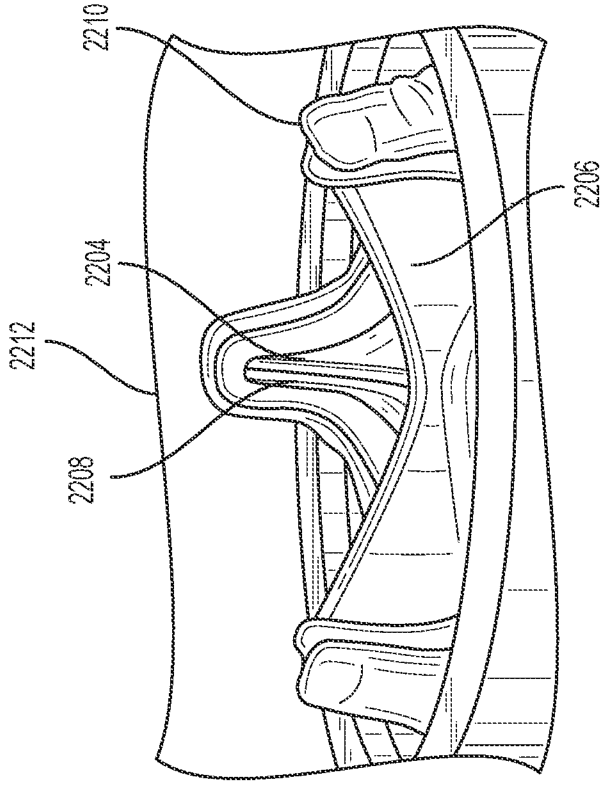
FIG. 22B illustrates a side view of a prosthetic heart valve according to an embodiment of the present disclosure.
Figure 22A:
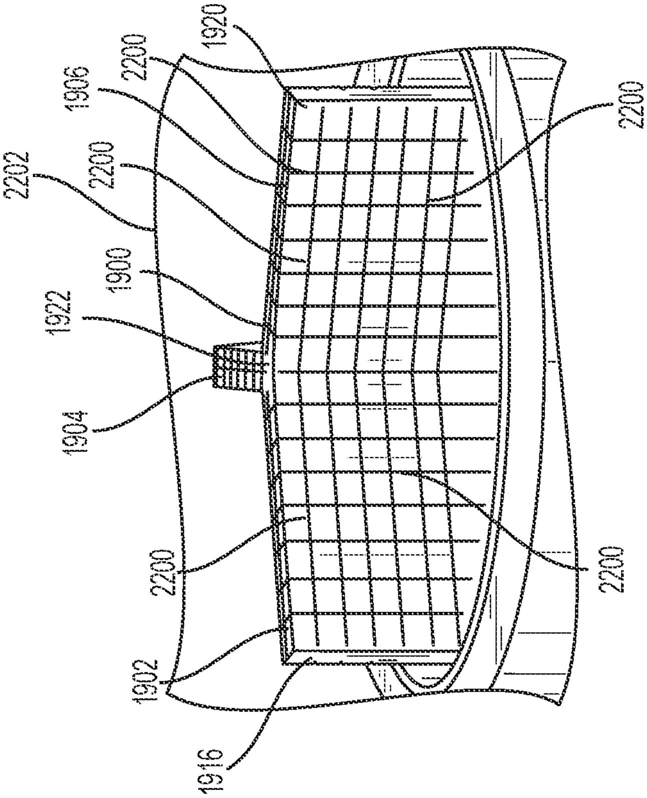
FIG. 22A illustrates a side view of a calibration device according to an embodiment of the present disclosure.

Each wall 1902, 1904, 1906 may include one or more indicators 2200 (marked in FIG. 22A). The indicators 2200 may be positioned on the side surfaces of the respective wall 1902, 1904, 1906 and/or the top surfaces 1930, 1932, 1934 of the respective wall 1902, 1904, 1906 (as shown in FIG. 20). The indicators 2200 are not shown in FIGS. 19 and 21 for clarity.

The indicators 2200 may indicate a position on the wall 1902, 1904, 1906. The indicators 2200 may be set at a defined real distance between each other, and a defined real distance between two indicators 2200 may be known. The real distance is the actual distance between the two indicators 2200, as may be measured in millimeters, inches, or another form of distance measurement.

The indicators 2200 may comprise a pattern, such as a grid, or other form of indicator 2200 with a known real distance between the indicators 2200. In one embodiment, at least one indicator 2200 may be utilized on at least one of the plurality of walls 1902, 1904, 1906. The indicators 2200 may be printed on the walls 1902, 1904, 1906 of the calibration device 1900, or may otherwise be placed on the walls 1902, 1904, 1906 (e.g., engraving or other form of placement).

Figure 23:
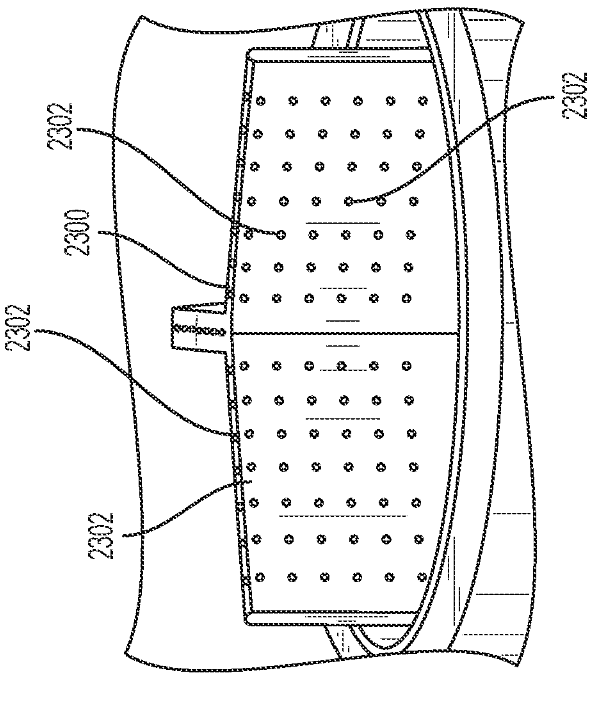
FIG. 23 illustrates a side view of a calibration device according to an embodiment of the present disclosure.

The indicators 2200 are preferably positioned on the calibration device 1900 at the central portion 1922 of the calibration device 1900 as well as at the end portions 1916, 1918, 1920 of the respective walls 1902, 1904, 1906. Such a positioning of the indicators 2200 may allow for a calibration of an image at a central portion of a prosthetic valve (such as the central opening 1710 shown in FIG. 17) as well as at a distal portion of prosthetic valve leaflets. The indicators may extend along the entirety of the calibration device 1900 from the central portion 1922 of the calibration device 1900 to the end portions 1916, 1918, 1920, as shown in FIGS. 22A and 23.

FIG. 20 illustrates a top view of the calibration device 1900. Top surfaces 1930, 1932, 1934 of the calibration device 1900 may include indicators 2200 for indicating a position on the respective wall 1902, 1904, 1906.

The calibration device 1900 and the walls 1902, 1904, 1906 may be configured to be coupled to at least a portion of the testing apparatus 100. For example, FIG. 21 illustrates an implementation of the calibration device 1900 with the test chamber 102 of the testing apparatus 100. The calibration device 1900 may be coupled to the wall 310 of the mounting plate 308 in a similar position and manner as the retainer ring 306 shown in FIG. 3. The walls 1902, 1904, 1906 may be positioned in the location of the leaflets of the valve 124 shown in FIG. 3, and may extend along the contact planes of the valve leaflets. The wall 118 may be positioned around the calibration device 1900 and the entire unit may be positioned in the testing apparatus 100 in a similar manner as discussed in regard to the test chamber 102 previously.

FIG. 22A illustrates an image 2202 of the calibration device 1900 including indicators 2200. The calibration device 1900 is preferably positioned in the testing apparatus 100 in the same location that the prosthetic valve will be positioned. The calibration device 1900 may be coupled to a retainer of the testing apparatus boo, with the walls 1902, 1904, 1906 positioned in the contact planes of the valve leaflets.

The image 2202 of the calibration device 1900 may be used to determine a scaling between an image distance and a real distance. The scaling may comprise a pixel to length ratio or other form of scaling. The image distance, as reflected in FIG. 22A, is the distance across the image 2202 between portions of the calibration device 1900. For example, the image distance may be measured in units of pixels or the like between two portions of the calibration device 1900. The image distance, however, may not accurately reflect the real distance (the actual distance) due to optical distortions and the cylindrical orientation of the prosthetic valve. For example, a measurement of 10 pixels at the central portion 1922 of the calibration device 1900 may not comprise the same real distance as 10 pixels at an end portion 1916 of the calibration device 1900.

As such, the defined real distance between the portions of the calibration device may be utilized to determine the scaling between the image distance and the real distance. For example, if a measurement of 10 pixels at the central portion 1922 of the calibration device 1900 is known to correspond to 1 millimeter (real distance), then the scaling between image distance and real distance may be determined at that portion of the calibration device 1900. Similarly, if a measurement of 10 pixels at an end portion 1916 of the calibration device 1900 is known to correspond to 2 millimeters (real distance), then the scaling between image distance and real distance may be determined at that portion of the calibration device 1900. The known distance between the portions of the calibration device 1900, particularly the indicators 2200, are utilized to determine the real distance. For example, if a distance of 10 pixels is measured between indicators 2200 known to have real distance of 1 millimeter, then the scaling of a 10:1 ratio of image distance to real distance may be determined.

Multiple scalings may be determined for multiple portions of the calibration device 1900. For example, a scaling may be determined between an image distance and a real distance based on an image distance between one or more portions of the calibration device at the central portion 1922. For the same image, a scaling may be determined between an image distance and a real distance based on an image distance between one or more portions of one of the plurality of walls 1902, 1904, 1906 at the end portion 1916, 1918, 1920 of the respective wall 1902, 1904, 1906. For the same image, the scaling may be determined for multiple positions on the calibration device 1900. The scaling may be different for each portion of the calibration device. As shown in FIG. 22A, the indicators 2200 may form a plurality of segments bounded by the indicators 2200 (bounded by the indicator lines), and a scaling may be provided for each segment of the calibration device 1900. The scaling may occur in both the X direction (horizontally across the page), and in the Y direction (vertically along the page). The indicators 2200 accordingly may extend along both the X direction and Y direction of the walls 1902, 1904, 1906.

Referring to FIG. 22B, the determined scaling may be utilized to determine a property of one or more leaflets 2204, 2206, 2208 of a prosthetic valve 2210 in an image 2212 of the prosthetic valve 2210. If an image distance is taken of a mismatch of the leaflets 2204, 2206, 2208, then this image distance may be converted to a real distance based on the scaling provided by the calibration device 1900. The image distance may be measured between portions of one or more leaflets 2204, 2206, 2208 of the prosthetic valve 2210 and a real distance may be determined between the portions of the one or more leaflets 2204, 2206, 2208 based on the scaling. For example, if a central portion of the prosthetic valve 2210 is measured and determined to have a leaflet mismatch of 10 pixels (image distance), then this image distance may be converted to the appropriate real distance based on the scaling provided by the calibration device 1900 for that portion. Similarly, if a distal portion of the prosthetic valve 2210 is measured and determined to have a leaflet mismatch of 10 pixels (image distance), then this image distance may be converted to the appropriate real distance based on the scaling provided by the calibration device 1900 for that portion. Multiple scalings may be provided for each portion of the image 2212.

The one or more of the cameras 414, 416, 184, 132 may be utilized to view both the calibration device 1900 and the prosthetic valve 2210. An axial view of the calibration device 1900 may also be provided, with a view of indicators positioned on an upper surface of the walls 1902, 1904, 1906. The calibration on the top surface 1930, 1932, 1934 of the calibration device 1900 may be used to determine a scaling of image distance to real distance in an axial image in a similar manner as discussed regarding the side images.

Multiple images of the calibration device 1900 may be provided (for example, three side views corresponding to the three leaflets of the prosthetic valve, and an axial image of the prosthetic valve) to determine a scaling between an image distance and a real distance for each leaflet of the prosthetic valve at each view.

Preferably, the angle of the images of the calibration device 1900 is the same as the angle of the corresponding images of the prosthetic valve 2210, to assure that the scaling is accurate for each view. Similarly, preferably the images of the calibration device 1900 are taken with the calibration device 1900 in the same position and surrounded by the same test fluid as the prosthetic valve 2210.

The processor 1100 may be configured to automatically determine the distance between the indicators 2200 of the calibration device 1900, and provide a scaling of image distance to real distance based on the determination.

The image or images of the calibration device 1900 may be stored in a memory, for example, the memory 1102 of the controller 114, for use to determine the real distance of the prosthetic valve 2210. The image or images 2202 of the calibration device 1900 may be taken on a periodic basis (e.g., daily, weekly, monthly basis). Preferably the one or more of the cameras 414, 416, 184, 132 do not move between taking images of the calibration device 1900 so that the view and angle of the calibration device 1900 may be same as the view of the actual prosthetic valve.

The scalings provided by the calibration device 1900 are preferably stored in a memory, for example, the memory 1102 of the controller 114, for use to convert image distance to real distance. The scalings may be set for a particular type of prosthetic device, and may be retrieved by a processor 1100 to automatically scale image distance to real distance based on the type of prosthetic device being viewed.

The calibration device 1900 may be utilized to provide a quantitative (rather than qualitative) measure of the coaptation of one or more leaflets of the prosthetic valve 2210. The quantitative measure may be provided because the real distance of the mismatch of the one or more leaflets of the prosthetic valve 2210 may be provided based on the measured image distance of the valve 2210 and the scaling provided by the calibration device 1900. The processor 1100 may be configured to output the determined real distance, and may be configured to output a ratio between the measured leaflet mismatch real distance vs. a desired or acceptable mismatch real distance. The processor 1100 may be configured to compare the measurement of the coaptation with a standard for acceptable coaptation, and provide an indication of whether the prosthetic valve is acceptable or not (for example, through the indicator 1110 discussed in regard to FIG. 1*i*). As discussed in regard to FIG. 16, the user may not make a determination of suitable coaptation in certain embodiments or in certain embodiments the user may confirm or make a separate determination of suitable coaptation based on viewing the images on the display screen 208 or the like.

In other embodiments, the calibration device 1900 may have a different form than shown. For example, FIG. 23 illustrates an embodiment of a calibration device 2300 in which the indicators 2302 may take the form of a plurality of dots on the walls of the calibration device 2300. The distance between the dots may be known. In other embodiments, other forms of indicators may be utilized.

The testing apparatus 100, and methods and device disclosed herein, may provide an efficient method of determining properties of prosthetic devices to be measured. A dual-drive configuration and physiological pulsatile operation of the testing apparatus 100 may allow for a more accurate measure of prosthetic device performance. A complete cardiac cycle may be provided for prosthetic heart valves, which may include a cycle, for example, of seventy beats per minute, and 100 millimeters mercury (mmHG) mean pressure, while a camera system monitors four coaptation test views (three side views and one axial view). The density of the test fluid may be approximate to blood passing through the prosthetic heart valves, and the test fluid may include water and glutaraldehyde (or a combination thereof) if desired, among other substances.

The calibration devices disclosed herein may provide for an improved calibration of image distance to real distance for a quantitative measure of valve quality.

The apparatuses, methods, and devices disclosed herein may be used in combination or substituted with each other as desired.

The apparatuses and other devices disclosed herein may be practiced separately as desired. In addition, the methods herein are not limited to the methods specifically described, and may include methods of utilizing the systems, apparatuses, and devices disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method comprising:

determining a scaling between an image distance and a real distance based on one or more images of a calibration device, the calibration device having a plurality of walls each extending radially outward from a central portion of the plurality of walls to an end portion of the respective wall, each of the plurality of walls extending axially to a top surface of the respective wall, the calibration device including a plurality of indicators on at least one of the plurality of walls, the plurality of indicators being spaced from each other at a defined real distance; and determining a property, based on the scaling, of one or more leaflets of a prosthetic valve shown in one or more images, and wherein each of the plurality of walls in the one or more images of the calibration device extend in a contact plane of the one or more leaflets.

2. The method of claim 1, wherein the property is a quantitative measure of a coaptation of the one or more leaflets.

3. The method of claim 2, wherein the quantitative measure is a real distance of a mismatch of the one or more leaflets.

4. The method of claim 1, wherein the calibration device includes a central portion and each of the plurality of walls extend radially outward from the central portion to a respective end portion.

5. The method of claim 4, wherein the scaling is a first scaling determined between an image distance and a real distance based on an image distance between one or more portions of the calibration device at the central portion; and the method further comprises determining a second scaling between an image distance and a real distance based on an image distance between one or more portions of one of the plurality of walls at the end portion of the respective wall.

6. The method of claim 5, wherein the one or more portions of the calibration device at the central portion include one or more of the plurality of indicators positioned on one or more of the plurality of walls, and the one or more portions of the plurality of walls at the end portion of the respective wall include one or more of the plurality of indicators positioned on the respective wall.

7. The method of claim 6, wherein a real distance is known between the one or more indicators of the central portion of the calibration device, and a real distance is known between the one or more indicators of the end portion of the respective wall.

8. The method of claim 5, wherein the first scaling is different than the second scaling.

9. The method of claim 1, wherein the scaling includes a pixel to length ratio.

10. The method of claim 1, further comprising measuring an image distance between portions of the one or more leaflets of the prosthetic valve and determining a real distance between the portions of the one or more leaflets of the prosthetic valve based on the scaling.

11. The method of claim 1, wherein one or more cameras provide the one or more images of the calibration device.

12. The method of claim 11, wherein the one or more cameras include a side camera and an axial camera, the side camera having a side view of the calibration device, and the axial camera having an axial view of the calibration device.

13. The method of claim 1, wherein the one or more images of the prosthetic valve are taken with the prosthetic valve positioned within a test chamber of a testing apparatus.

14. The method of claim 13, wherein the testing apparatus is configured to provide pulsatile flow through the prosthetic valve.

15. The method of claim 13, further comprising operating the testing apparatus to determine a leakage of the prosthetic valve or to determine an effective orifice area of the prosthetic valve.

16. The method of claim 13, wherein the one or more images of the calibration device are taken with the calibration device positioned within the test chamber of the testing apparatus.

17. The method of claim 1, wherein the prosthetic valve is a prosthetic heart valve.

18. The method of claim 1, wherein the plurality of indicators comprise a pattern on the at least one of the plurality of walls.

19. The method of claim 1, wherein the plurality of walls includes at least three walls.

20. The method of claim 1, wherein the plurality of walls are static relative to each other.

* * * * *